(12) United States Patent
Genovese et al.

(10) Patent No.: US 9,835,631 B2
(45) Date of Patent: *Dec. 5, 2017

(54) COMBINED BIOMARKER MEASUREMENT OF FIBROSIS

(71) Applicants: Federica Genovese, Frederiksberg (DK); Mette Juul Nielsen, Copenhagen (DK); Lise Larsen, Kastrup (DK); Diana Julie Oersnes-Leeming, Espergæde (DK); Morten Karsdal, Copenhagen (DK)

(72) Inventors: Federica Genovese, Frederiksberg (DK); Mette Juul Nielsen, Copenhagen (DK); Lise Larsen, Kastrup (DK); Diana Julie Oersnes-Leeming, Espergæde (DK); Morten Karsdal, Copenhagen (DK)

(73) Assignee: Nordic Bioscience A/S, Herlev (DK)

( * ) Notice: Subject to any disclaimer, the term of this patent is extended or adjusted under 35 U.S.C. 154(b) by 0 days.

This patent is subject to a terminal disclaimer.

(21) Appl. No.: 15/014,241

(22) Filed: Feb. 3, 2016

(65) Prior Publication Data

US 2016/0223568 A1   Aug. 4, 2016

Related U.S. Application Data

(63) Continuation-in-part of application No. 14/784,512, filed as application No. PCT/EP2014/057597 on Apr. 15, 2014, now Pat. No. 9,726,674.

(30) Foreign Application Priority Data

Apr. 15, 2013 (GB) .................................. 1306792.1

(51) Int. Cl.
*G01N 33/53* (2006.01)
*G01N 33/68* (2006.01)
*G01N 33/577* (2006.01)

(52) U.S. Cl.
CPC ....... *G01N 33/6893* (2013.01); *G01N 33/577* (2013.01); *G01N 2333/78* (2013.01); *G01N 2800/085* (2013.01); *G01N 2800/52* (2013.01); *G01N 2800/7052* (2013.01)

(58) Field of Classification Search
None
See application file for complete search history.

(56) References Cited

U.S. PATENT DOCUMENTS

| | | | |
|---|---|---|---|
| 2007/0172907 A1* | 7/2007 | Volker | C12Q 1/6883 435/15 |
| 2009/0143993 A1* | 6/2009 | Cales | G01N 33/576 702/19 |
| 2009/0150315 A1* | 6/2009 | Wirtz | C12Q 1/6886 706/46 |

* cited by examiner

*Primary Examiner* — Jacob Cheu
(74) *Attorney, Agent, or Firm* — Benjamin Aaron Adler

(57) ABSTRACT

Provided herein is a sandwich immunoassay for detecting cross-linked PIIINP that has at least two strands of PIIINP joined together by inter-strand cross-linking each having a C-terminal neo-epitope of PIIINP that is generated by N-protease cleavage of intact type III procollagen. A biological sample having the cross-linked PIIINP is contacted with a first surface-bound monoclonal antibody and then by a second monoclonal antibody, both specifically reactive with a neoepitope in the C-terminal sequence of PIIINP, and then binding of the second monoclonal antibody is determined. Also provided is a method for evaluating the efficacy of an antagonist drug targeting lysyl oxidases via the immunoassay and a kit containing a solid support binding the first monoclonal antibody and containing the second monoclonal antibody.

14 Claims, 17 Drawing Sheets

CLUSTAL O (1.1.0) multiple sequence alignment

Figure 2:
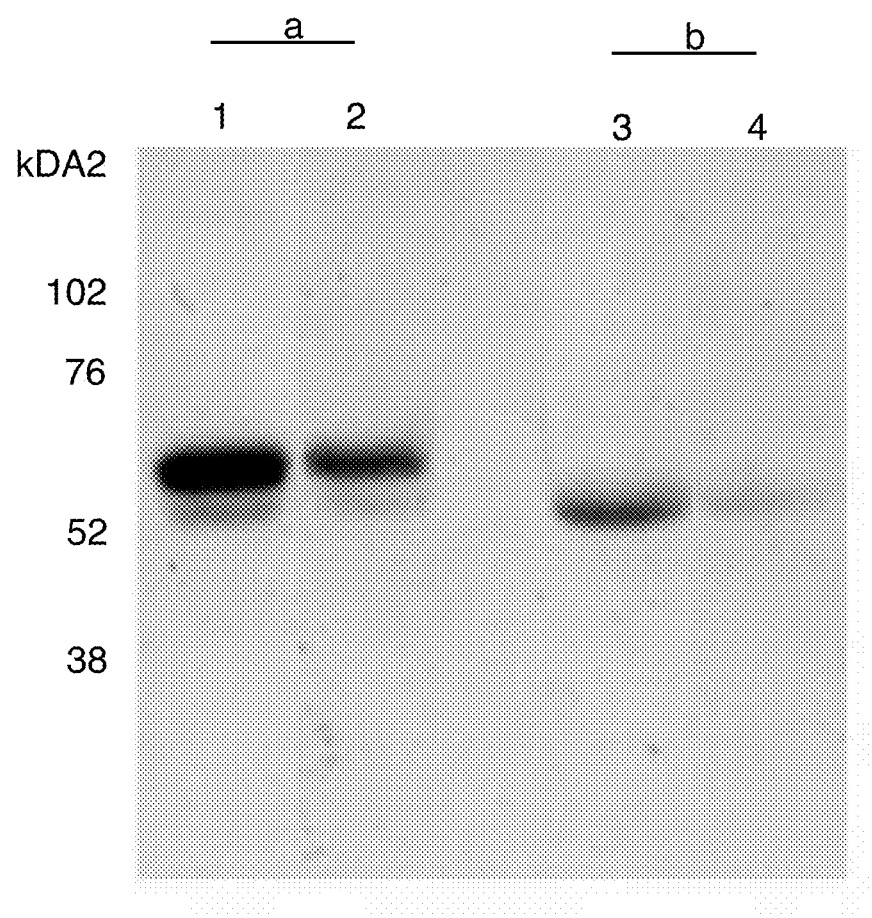

```
sp|P02461CO3a1_HUMAN     MMSFVQKGSWLLLALLHPTIIIAQQFAV-E 29
sp|P13941CO3a1_RAT       MMSFVQCGTWFLLTLLHPSLIIAQQSNVDE 30
                         ****** *:*::::***. * * sp|P02461CO3a1_HUMAN     GGCSHLGQSYADRDVWKPEPCQICVCDSGS 59
sp|P13941CO3a1_RAT       LGCNYLGQSYESRDVWKPEPCQICVCDSGS 60
                         **.:****** .******************
sp|P02461CO3a1_HUMAN     VLCDDIICDDQELDCPNPEIPFGECCAVCP 89
sp|P13941CO3a1_RAT       VLCDDIMCDDEPLDCPNPEIPFGECCAICP 90
                         ******:***: **************:**
sp|P02461CO3a1_HUMAN     QPPTAPTRPPNGQGPQGPKGDPGPPGIPGR 119
sp|P13941CO3a1_RAT       QPSTPAPVIPDGNRPQGPKGDPGPPGIPGR 120
                         ** *          *:*: ********** sp|P02461CO3a1_HUMAN     NGDPGIPGQPGSPGSPGPPGICFSCPTGPQ 149
sp|P13941CO3a1_RAT       NGDPGLPGQPGLPGPPGSPGICESCPTGGQ 150
                         ***:*   ******* * sp|P02461CO3a1_HUMAN     NYSPQYDSYDVKSGVAVGGLAGYPGPAGPP 179
sp|P13941CO3a1_RAT       NYSPQFDSYDVKSG--VGGMGGVPGPAGPP 178
                         **:****   *:.******** sp|P02461CO3a1_HUMAN     SEQ ID NO: 14
sp|P13941CO3a1_RAT       SEQ ID NO: 15
```

FIG. 1

```
                        SEQUENCE LISTING

<160> NUMBER OF SEQ ID NOS: 15

<210> SEQ ID NO 1
<211> LENGTH: 14
<212> TYPE: PRT
<213> ORGANISM: Artificial Sequence
<220> FEATURE:
<223> OTHER INFORMATION: modified bovine PIIINP C-terminal sequence
<220> FEATURE:
<221> NAME/KEY: misc_feature
<222> LOCATION: (2)
<223> OTHER INFORMATION: acetamido protected Cys
<220> FEATURE:
<221> NAME/KEY: misc_feature
<222> LOCATION: (10)
<223> OTHER INFORMATION: Glu replaces Gln at position 10

<400> SEQUENCE: 1

Ile Cys Gln Ser Cys Pro Thr Gly Gly Glu Asn Tyr Ser Pro
1               5                   10

<210> SEQ ID NO 2
<211> LENGTH: 14
<212> TYPE: PRT
<213> ORGANISM: Bos sp.
<220> FEATURE:
<223> OTHER INFORMATION: Bovine PIIINP C-terminal sequence

<400> SEQUENCE: 2

Ile Cys Gln Ser Cys Pro Thr Gly Gly Gln Asn Tyr Ser Pro
1               5                   10

<210> SEQ ID NO 3
<211> LENGTH: 21
<212> TYPE: PRT
<213> ORGANISM: Homo sapiens
<220> FEATURE:
<223> OTHER INFORMATION: Human C-terminal PIIINP sequence

<400> SEQUENCE: 3

Gly Ser Pro Gly Pro Pro Gly Ile Cys Gln Ser Cys Pro Thr Gly Pro
1               5                   10                  15

Gln Asn Tyr Ser Pro
            20

<210> SEQ ID NO 4
<211> LENGTH: 10
<212> TYPE: PRT
<213> ORGANISM: Artificial sequence
<220> FEATURE:
<223> OTHER INFORMATION: C-terminal PIIINP neo-epitope sequence
```

```
<220> FEATURE:
<221> NAME/KEY: misc_feature
<222> LOCATION: (5)
<223> OTHER INFORMATION: Xaa is Pro or Gly

<400> SEQUENCE: 4

Cys Pro Thr Gly Xaa Gln Asn Tyr Ser Pro
1               5                   10

<210> SEQ ID NO 5
<211> LENGTH: 12
<212> TYPE: PRT
<213> ORGANISM: Artificial sequence
<220> FEATURE:
<223> OTHER INFORMATION: C-terminal elongation of SEQ ID NO: 4
<220> FEATURE:
<221> NAME/KEY: misc_feature
<222> LOCATION: (5)
<223> OTHER INFORMATION: Xaa is Pro or Gly
<220> FEATURE:
<221> NAME/KEY: misc_feature
<222> LOCATION: (12)
<223> OTHER INFORMATION: Xaa is absent or is one or more amino acids of
      the sequence of collagen type III

<400> SEQUENCE: 5

Cys Pro Thr Gly Xaa Gln Asn Tyr Ser Pro Gln Xaa
1               5                   10

<210> SEQ ID NO 6
<211> LENGTH: 10
<212> TYPE: PRT
<213> ORGANISM: Artificial sequence
<220> FEATURE:
<223> OTHER INFORMATION: PIIINP C-terminal selection peptide sequence

<400> SEQUENCE: 6

Cys Pro Thr Gly Pro Gln Asn Tyr Ser Pro
1               5                   10

<210> SEQ ID NO 7
<211> LENGTH: 10
<212> TYPE: PRT
<213> ORGANISM: Rattus sp.
<220> FEATURE:
<223> OTHER INFORMATION: Rodent PIIINP neo-epitope C-terminal sequence

<400> SEQUENCE: 7

Cys Pro Thr Gly Gly Gln Asn Tyr Ser Pro
1               5                   10

<210> SEQ ID NO 8
<211> LENGTH: 9
<212> TYPE: PRT
<213> ORGANISM: Artificial Sequence
<220> FEATURE:
<223> OTHER INFORMATION: Human C-terminal PIIINP neo-epitope sequence
<220> FEATURE:
<221> NAME/KEY: misc_feature
<222> LOCATION: (5)
<223> OTHER INFORMATION: Xaa can be Pro or Gly

<400> SEQUENCE: 8

Cys Pro Thr Gly Xaa Gln Asn Tyr Ser
1               5

<210> SEQ ID NO 9
<211> LENGTH: 13
<212> TYPE: PRT
```

```
<213> ORGANISM: Artificial Sequence
<220> FEATURE:
<223> OTHER INFORMATION: Modified C-terminal PIIINP peptide
<220> FEATURE:
<221> NAME/KEY: misc_feature
<222> LOCATION: (1)..(3)
<223> OTHER INFORMATION: Xaa Xaa Xaa is absent or is a Cys Gly Gly
      linker where Cys at position 1 is modified with biotin
<220> FEATURE:
<221> NAME/KEY: misc_feature
<222> LOCATION: (4)
<223> OTHER INFORMATION: Cys is biotinylated if Xaa Xaa Xaa is absent

<400> SEQUENCE: 9

Xaa Xaa Xaa Cys Pro Thr Gly Pro Gln Asn Tyr Ser Pro
1               5                   10

<210> SEQ ID NO 10
<211> LENGTH: 13
<212> TYPE: PRT
<213> ORGANISM: Artificial Sequence
<220> FEATURE:
<223> OTHER INFORMATION: modified PIIINP C-terminal immunogenic peptide
      with linker
<220> FEATURE:
<221> NAME/KEY: misc_feature
<222> LOCATION: (1)...(3)
<223> OTHER INFORMATION: N-terminal linker sequence
<220> FEATURE:
<221> NAME/KEY: misc_feature
<222> LOCATION: (1)
<223> OTHER INFORMATION: Cys has N-terminal bound ovalbumin

<400> SEQUENCE: 10

Cys Gly Gly Cys Pro Thr Gly Pro Gln Asn Tyr Ser Pro
1               5                   10

<210> SEQ ID NO 11
<211> LENGTH: 13
<212> TYPE: PRT
<213> ORGANISM: Artificial Sequence
<220> FEATURE:
<223> OTHER INFORMATION: modified PIIINP C-terminal screening peptide
      with linker
<220> FEATURE:
<221> NAME/KEY: misc_feature
<222> LOCATION: (1)...(3)
<223> OTHER INFORMATION: N-terminal linker sequence
<220> FEATURE:
<221> NAME/KEY: misc_feature
<222> LOCATION: (1)
<223> OTHER INFORMATION: Cys has N-terminal bound biotin

<400> SEQUENCE: 11

Cys Gly Gly Cys Pro Thr Gly Pro Gln Asn Tyr Ser Pro
1               5                   10

<210> SEQ ID NO 12
<211> LENGTH: 10
<212> TYPE: PRT
<213> ORGANISM: Artificial Sequence
<220> FEATURE:
<223> OTHER INFORMATION: Non-sense peptide for ELISA

<400> SEQUENCE: 12

Gly Ser Pro Gly Lys Asp Gly Val Arg Gly
1               5                   10

<210> SEQ ID NO 13
<211> LENGTH: 11
<212> TYPE: PRT
```

-continued

```
<213> ORGANISM: Artificial Sequence
<220> FEATURE:
<223> OTHER INFORMATION: C-terminal elongation of SEQ ID NO: 6

<400> SEQUENCE: 13

Cys Pro Thr Gly Pro Gln Asn Tyr Ser Pro Gln
1               5                   10

<210> SEQ ID NO 14
<211> LENGTH: 179
<212> TYPE: PRT
<213> ORGANISM: Homo sapiens
<220> FEATURE:
<223> OTHER INFORMATION: Human PIIINP alpha1 chain sequence

<400> SEQUENCE: 14

Met Met Ser Phe Val Gln Lys Gly Ser Trp Leu Leu Leu Ala Leu
1               5                   10                  15

Leu His Pro Thr Ile Ile Ile Ala Gln Gln Phe Ala Val Glu Gly
                20                  25                  30

Gly Cys Ser His Leu Gly Gln Ser Tyr Ala Asp Arg Asp Val Trp
                35                  40                  45

Lys Pro Glu Pro Cys Gln Ile Cys Val Cys Asp Ser Gly Ser Val
                50                  55                  60

Leu Cys Asp Asp Ile Ile Cys Asp Asp Gln Glu Leu Asp Cys Pro
                65                  70                  75

Asn Pro Glu Ile Pro Phe Gly Glu Cys Cys Ala Val Cys Pro Gln
                80                  85                  90

Pro Pro Thr Ala Pro Thr Arg Pro Pro Asn Gly Gln Gly Pro Gln
                95                  100                 105

Gly Pro Lys Gly Asp Pro Gly Pro Gly Ile Pro Gly Arg Asn
                110                 115                 120

Gly Asp Pro Gly Ile Pro Gly Gln Pro Gly Ser Pro Gly Ser Pro
                125                 130                 135

Gly Pro Pro Gly Ile Cys Phe Ser Cys Pro Thr Gly Pro Gln Asn
                140                 145                 150

Tyr Ser Pro Gln Tyr Asp Ser Tyr Asp Val Lys Ser Gly Val Ala
                155                 160                 165

Val Gly Gly Leu Ala Gly Tyr Pro Gly Pro Ala Gly Pro Pro
                170                 175

<210> SEQ ID NO 15
<211> LENGTH: 178
<212> TYPE: PRT
<213> ORGANISM: Rattus sp.
<220> FEATURE:
<223> OTHER INFORMATION: Rat PIIINP alpha1 chain sequence

<400> SEQUENCE: 15

Met Met Ser Phe Val Gln Cys Gly Thr Trp Phe Leu Leu Thr Leu
1               5                   10                  15

Leu His Pro Ser Leu Ile Ile Ala Gln Gln Ser Asn Val Asp Glu
                20                  25                  30

Leu Gly Cys Asn Tyr Leu Gly Gln Ser Tyr Glu Ser Arg Asp Val
                35                  40                  45

Trp Lys Pro Glu Pro Cys Gln Ile Cys Val Cys Asp Ser Gly Ser
                50                  55                  60

Val Leu Cys Asp Asp Ile Met Cys Asp Asp Glu Pro Leu Asp Cys
                65                  70                  75
```

```
Pro Asn Pro Glu Ile Pro Phe Gly Glu Cys Cys Ala Ile Cys Pro
                80              85              90

Gln Pro Ser Thr Pro Ala Pro Val Ile Pro Asp Gly Asn Arg Pro
                95              100             105

Gln Gly Pro Lys Gly Asp Pro Gly Pro Gly Ile Pro Gly Arg
                110             115             120

Asn Gly Asp Pro Gly Leu Pro Gly Gln Pro Gly Leu Pro Gly Pro
                125             130             135

Pro Gly Ser Pro Gly Ile Cys Glu Ser Cys Pro Thr Gly Gly Gln
                140             145             150

Asn Tyr Ser Pro Gln Phe Asp Ser Tyr Asp Val Lys Ser Gly Val
                155             160             165

Gly Gly Met Gly Gly Val Pro Gly Pro Ala Gly Pro Pro
                170             175
```

COMBINED BIOMARKER MEASUREMENT OF FIBROSIS

BACKGROUND OF THE INVENTION

Technical Field of the Invention

The present invention relates in a first aspect to a monoclonal antibody which is specifically reactive with the C-terminal neo-epitope of PIIINP, and its use in a method of immunoassay for detecting and quantifying PIIINP. In a further aspect, the invention relates to a sandwich immunoassay for detecting in a biological sample cross-linked PIIINP, and its use in evaluating the efficacy of drugs targeting lysyl oxidases (LOXs).

Description of the Related Art

Fibrotic diseases (including those listed in Table 1) are a leading cause of morbidity and mortality, e.g. cirrhosis with 800,000 deaths per year worldwide (1).

TABLE 1

Different fibrotic diseases (2).

| Tissue | Examples of Causes |
| --- | --- |
| Liver | Viral hepatitis |
| | Schistosomiasis |
| | Steatohepatitis (Alcoholic or non-alcoholic) |
| Lung | Idiopathic pulmonary fibrosis (IPF) |
| | Systemic sclerosis (Scleroderma) |
| Kidney | Nephrogenic systemic fibrosis (NSF) |
| | Diabetes |
| | Untreated hypertension |
| Heart | Heart attack |
| | Hypertension |
| | Atherosclerosis |
| | Restenosis |
| Eye | Macular degeneration, retinal and vitreal retinopathy |
| Skin | Systemic sclerosis and scleroderma, keloids, hypertrophic scars, burns, genetic factors NFS |
| Pancreas | Autoimmune/hereditary causes |
| Intestine | Crohn's disease/inflammatory bowel disease |
| Brain | Alzheimer's disease, AIDS |
| Bone marrow | Cancer, ageing |
| Multi-organ fibrosis | Surgical complications, chemotherapeutic drug-induced fibrosis, radiation-induced fibrosis, mechanical injuries |

A 'fibrotic disease' is any disease giving rise to fibrosis, whether as a main or a secondary symptom. Fibrosis is the end result of chronic inflammatory reactions induced by a variety of stimuli including persistent infections, autoimmune reactions, allergic responses, chemical insults, radiation, and tissue injury. Fibrosis is characterized by the accumulation and reorganization of the extracellular matrix (ECM). Despite having obvious etiological and clinical distinctions, most chronic fibrotic disorders have in common a persistent irritant that sustains the production of growth factors, proteolytic enzymes, angiogenic factors, and fibrogenic cytokines, which together stimulate the deposition of connective tissue elements, especially collagens and proteoglycans, which progressively remodel and destroy normal tissue architecture (3,4). Despite its enormous impact on human health, there are currently no approved treatments that directly target the mechanisms of fibrosis (5).

Extracellular Matrix (ECM)

The ECM is a supramolecular structure with the ability to form aggregates of proteins, thus forming a dynamic scaffold linking cells together in a three dimensional network. This scaffold controls cell-matrix interactions and cell fate through up and down regulation of proteases (6). The ECM consists of collagens, laminins, proteoglycans, and other glycoproteins in various amounts and combinations, thereby providing a variety of biological components which can be modified by proteases to produce scaffolds with specific functions to meet the needs of the individual tissue (7).

Collagen types I and III are the major structural proteins in the human body. Collagen type III is essential for collagen type I fibrillogenesis in the cardiovascular system and other organs (8,9). During fibrillar assembly the N-terminal propeptide of type III procollagen (which consists of three identical α-chains with a total molecular weight of 42 kDa) is cleaved off by specific N-proteases prior to incorporation of the mature collagen in the ECM. The cleaved propeptides may either be retained in the ECM or released into the circulation. However, the cleavage of the propeptide is sometimes incomplete, leaving the propeptide attached to the molecule. This results in the formation of thin fibrils with abnormal cross-links, which in turn causes the abnormal molecule to be prone to rapid metabolic turnover (10,11). Thus, the level of the N-terminal propeptide of type III collagen (PIIINP) in a suitable sample can be a marker of formation and/or degradation of collagen type III.

Remodeling of the ECM plays an important role in the pathogenesis of various diseases as altered components and non-coded modifications of the ECM leads to tissue stiffness and changes in the signaling potential of the intact ECM and fragments thereof. ECM remodeling is an important prerequisite for tissue function and repair, and is tightly controlled by the enzymes responsible for the synthesis and degradation of the ECM.

During pathological events, such as fibrotic diseases, the balance between the formation and the degradation of the ECM is disturbed, leading to an altered composition of the ECM. Such an alteration results in altered tissue function (12,13). It has been suggested that PIIINP could be used as a biomarker for several fibrotic diseases, such as lung injury (14), viral and non-viral hepatitis (15), systemic sclerosis (16), vascular remodeling (17), and kidney diseases (18).

Limited attention has been given to the ECM remodeling in skeletal muscle tissue. In rat models increased collagen gene expression and biosynthesis have been demonstrated in quadriceps femoris and tibialis anterior muscles after exercise (19,20). Additionally, increased serum levels of PIIINP have been demonstrated in clinical studies after exercise (21). Therefore, remodeling of the skeletal muscle proteins increases the quantity of PIIINP in the circulation and may serve as a biomarker for detecting early muscle anabolism. Serum levels of PIIINP have previously been suggested as a biomarker of muscular tissue response to testosterone (22), recombinant human growth hormone (23) or the combination thereof (24,25).

In liver fibrosis the fibrillar collagens type I and III are highly up-regulated (26,27). Type III collagen is dominant in the early stages of fibrosis, while up-regulation of type I collagen is related to the later stages of fibrosis. Fibrosis occurring in the liver results in the deposition of collagen and release of propeptides, predominantly PIIINP. Consequently, PIIINP is one of the best studied markers for fibrogenesis (28,29,30). Through the years, several radioimmunoassays have been developed for the quantification of PIIINP, with a sensitivity of up to 94% and specificity of up to 81% for the detection of cirrhosis (31,32); however none of the previous assays are neo-epitope specific. Additionally, the current commercially available assays for quantification of PIIINP utilise polyclonal antibodies or monoclonal antibodies targeting internal sequences of the procollagen or the propeptide and do not specifically differentiate between the formation and/or degradation of collagen type III (31,32).

Thus, to differentiate between formation and degradation of collagen type III we consider that it is necessary to determine and detect a neo-epitopic fragment which is solely produced in the formation process (i.e. a fragment which is produced in the formation of collagen type III but not produced in the degradation of collagen type III).

Herein is disclosed a monoclonal antibody which is specific for the C-terminal PIIINP neo-epitope comprised in the terminal amino acids of the C-terminal amino acid sequence CPTGXQNYSP-COOH (SEQ ID NO:4), wherein X can be Gly or Pro.

Brocks (31) discloses a polyclonal antibody directed to the modified Bovine C-terminal PIIINP sequence I C*QSCPTGG<u>E</u>NYSP-COON (SEQ ID NO: 1) (C*=acetamido protected Cys; Gln replaced with Glu (<u>E</u>)), however said antibodies are non-specific towards the terminal amino acids of the bovine PIIINP C-terminal sequence ICQSCPTGGQNYSP-COOH (SEQ ID NO: 2) and additionally said antibodies do not recognise human PIIINP.

Bayer (33) discloses a sandwich ELISA which utilises a detector monoclonal antibody directed to the sequence $H_2N$-GSPGPPGICQSCPTGPQNYSP-COOH (SEQ ID NO: 3), however the binding epitope is not defined.

Thus, the aim of the present invention is to provide a neo-epitope specific antibody directed towards the C-terminal neo-epitope of PIIINP and which is specific for its terminal character for use in a method of immunoassay for evaluating the disease severity of various fibrotic diseases.

The applicant has also found that a specific sandwich immunoassay which utilises the neo-epitope specific antibody directed towards the C-terminal neo-epitope of PIIINP may be useful in evaluating the efficacy of drugs that target lysyl oxidases (LOXs), particularly LOX antagonist drugs. Enzymatic collagen crosslinking by LOXs and processing of pro-collagens is key for tissue maturation and stability. In patients with organ fibrosis collagens become highly cross-linked, and thus are less prone to fibrosis resolution. LOXL2, a specific LOX, is a main driver in pathophysiological collagen crosslinking in fibrotic tissue, and novel LOXL2 antagonists are currently undergoing clinical trials. Thus, an assay that could be used to evaluate the efficacy of drugs targeting LOXs, such as LOX antagonists, would clearly be a useful tool for the pharmaceutical industry.

SUMMARY

The present invention is directed to a sandwich immunoassay for detecting in a biological sample cross-linked PIIINP where the cross-linked PIIINP comprises at least two strands of PIIINP joined together by inter-strand cross-linking. The method comprises contacting the biological sample comprising the cross-linked PIIINP with a first monoclonal antibody bound to a surface, where each strand of PIIINP comprised in the cross-linked PIIINP has a C-terminal neo-epitope of PIIINP generated by N-protease cleavage of intact type III procollagen and adding a second monoclonal antibody. Determining where both monoclonal antibodies are specifically reactive with the C-terminal neo-epitope of PIIINP and where the neo-epitope comprises a C-terminal amino acid sequence CPTGXQNYSP-COOH, where X is Gly or Pro. The amount of binding of the second monoclonal antibody is determined.

The present invention also is directed to a method for evaluating the efficacy of an antagonist drug targeting lysyl oxidases (LOXs). The method comprises using the sandwich immunoassay as described herein to quantify the amount of cross-linked PIIINP in at least two biological samples obtained from a subject at a first time point and at least one subsequent time point during a period of administration of the antagonist drug to the subject. A reduction in the quantity of cross-linked PIIINP from the first time point to the at least one subsequent time point during the period of administration of the antagonist drug is indicative of an efficacious antagonist drug targeting LOXs.

The present invention is directed further to a kit for use in the sandwich immunoassay as described herein. The kit comprises a solid support to which is bound the first monoclonal antibody as described above and a labelled second monoclonal antibody as described herein.

FIGURES

FIG. 1: Alignment of the targeted PIIINP α1 chain sequence in human (SEQ ID NO: 14) and rat (SEQ ID NO: 15) species (highlighted by the box). Position of the corresponding human (—) and rat (- - -) sequences within the alpha 1 chain of the N-terminal pro-peptide of type III collagen. The alignment was performed using the NLP CLUSTALW software.

FIG. 2: Western Blot showing the specific bands of N-terminal propeptide of type III collagen in Amniotic fluid from a) rat and b) human recognized by the monoclonal antibody NB61N62 (lane 1 and 3) and NB61N62+selection peptide (lane 2+4). Two bands around 52-60 kDA was observed for the rat, whereas one band was observed for human. Addition of selection peptide resulted in weakness of band intensity for both rat and human.

Figure 3A:
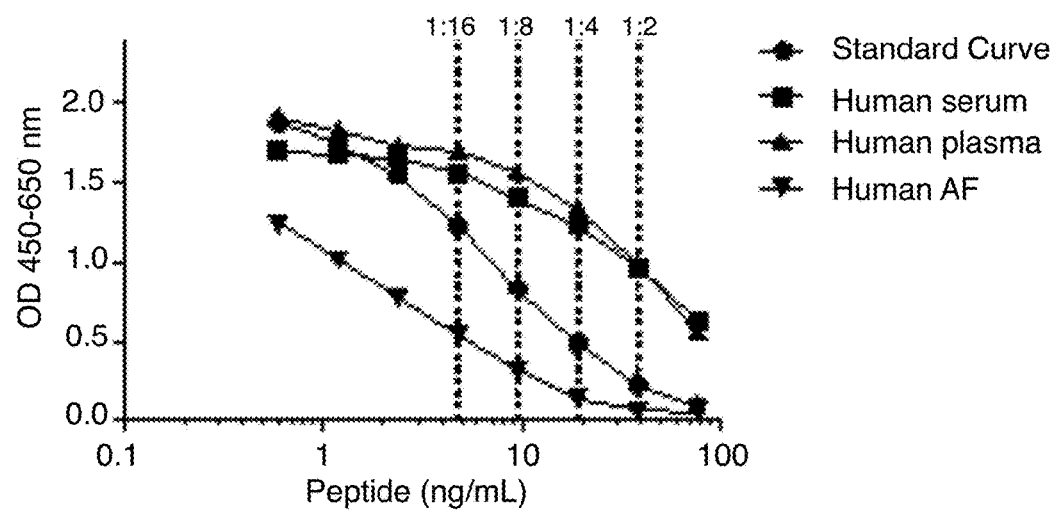
Figure 3B:
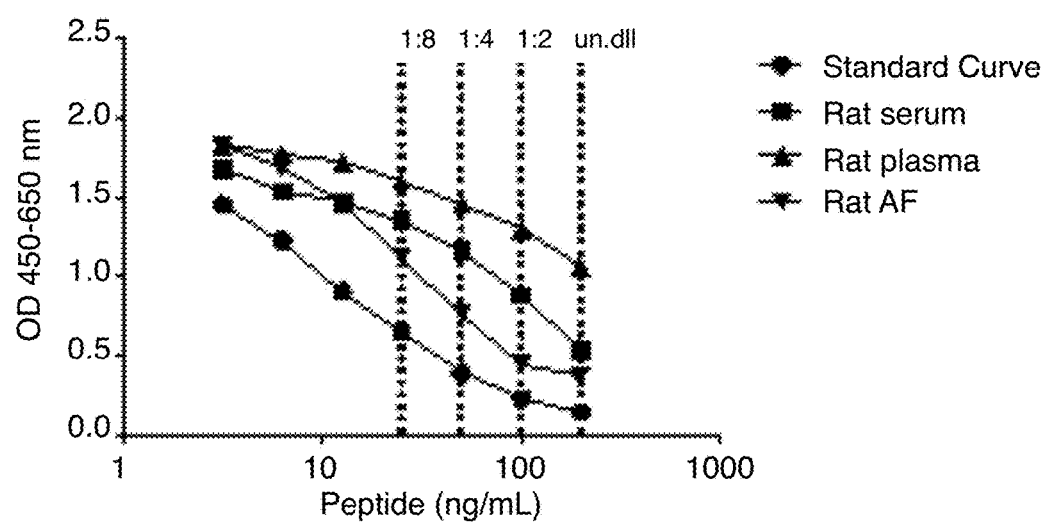
Figure 3C:
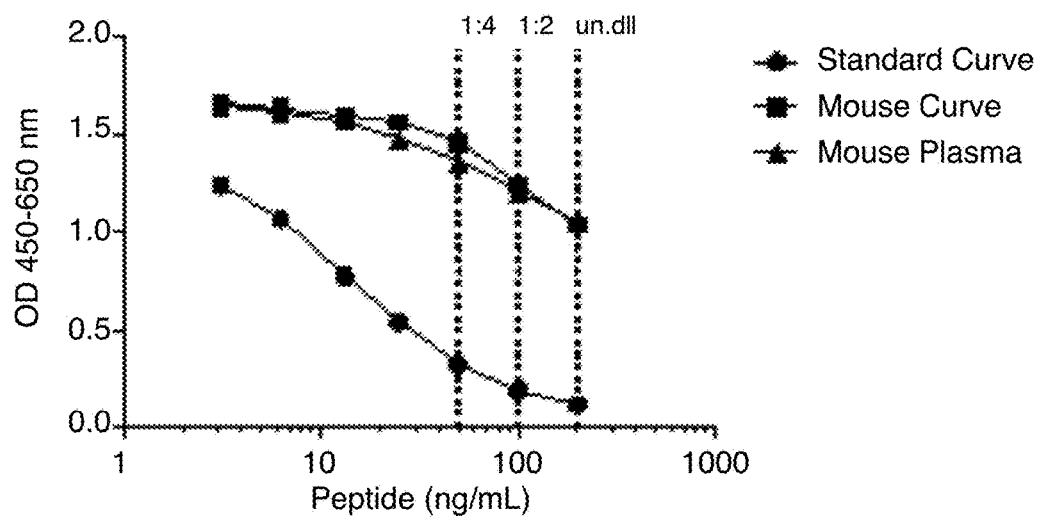
Figure 3D:
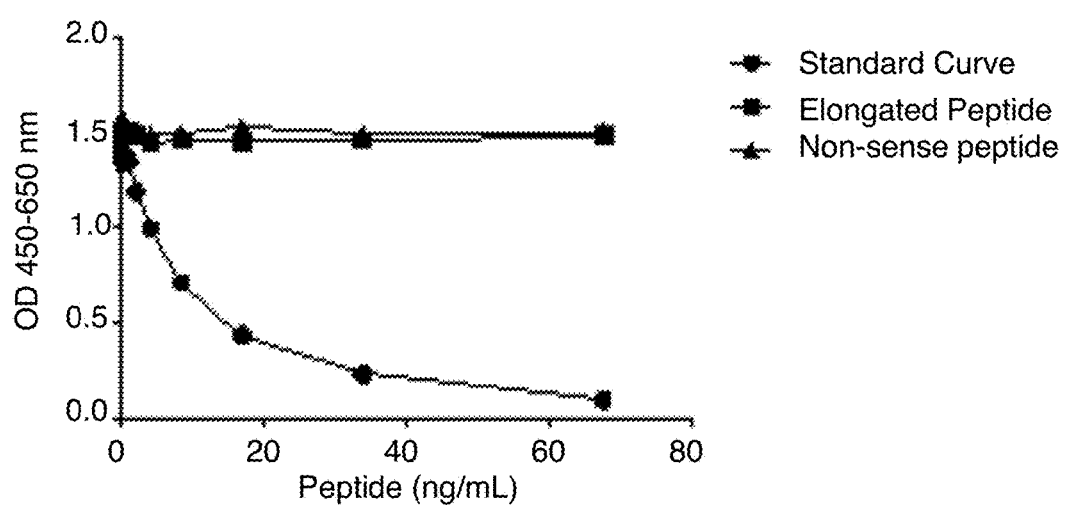

FIGS. 3A-3D: PRO-C3 ELISA runs showing typical calibration curves and native reactivity against human, rodent, and mouse material. FIG. 3A: Calibration curve and inhibition of the competitive PRO-C3 ELISA using healthy human serum, plasma, and amniotic fluid (AF). The calibrator curve was diluted in 2-fold from 76.31 ng/mL, whereas native material was run diluted 1:2 to 1:16 as indicated (--). FIG. 3B: Calibration curve and inhibition of the competitive PRO-C3 ELISA using healthy rat serum, plasma, and AF. The calibrator curve was diluted in 2-fold from 200 ng/mL, whereas native material was run undiluted to 1:8 as indicated (--). FIG. 3C: Calibration curve and inhibition of the competitive PRO-C3 ELISA using healthy mouse serum and plasma. The calibrator curve was diluted in 2-fold from 200 ng/mL, whereas native material was run undiluted to 1:4 as indicated (--). FIG. 3D: Neo-epitope specificity of the PIIINP neo-epitope specific antibody using elongated peptide, i.e. peptide sequence of calibration peptide with one additional amino acid in the C-terminal end. The calibration curve, elongated peptide, and non-sense peptide were diluted in 2-fold from 76.31 ng/mL. The signal is seen as the optical density at 450 nm, subtracting the background at 650 nm, as a function of peptide concentration.

Figure 4A:
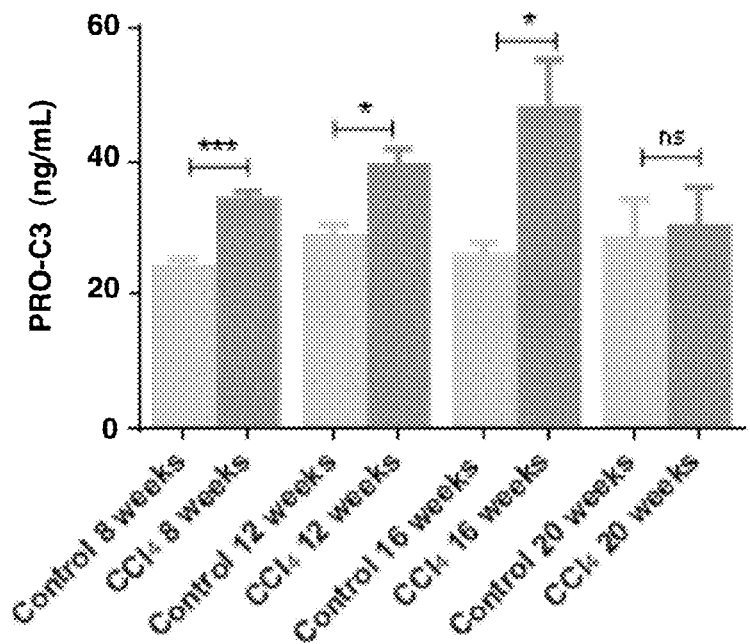
Figure 4B:
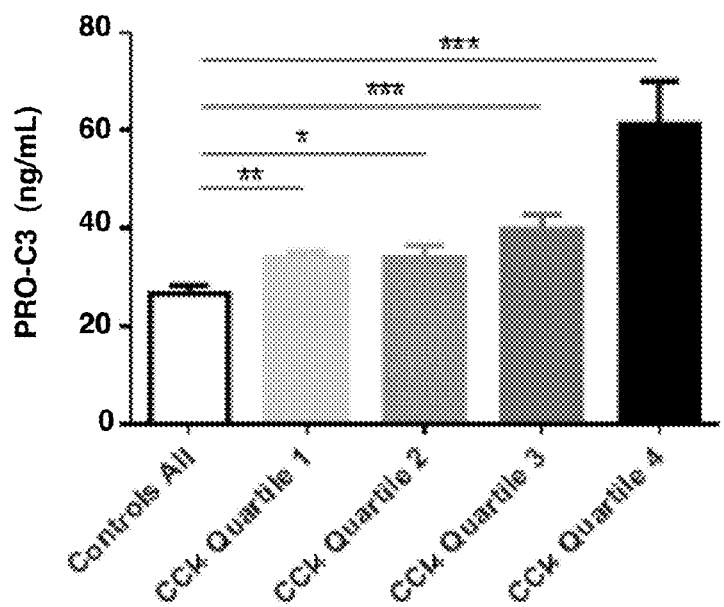
Figures 4C, 4D:
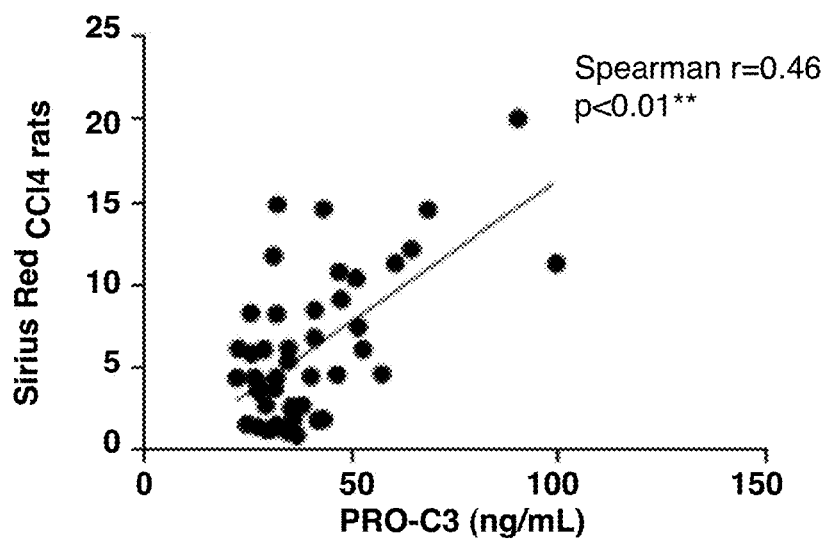

FIGS. 4A-4D: PIIINP levels measured in the $CCl_4$ inhalation rat model. FIG. 4A: Serum levels of PIIINP was assessed using the PRO-C3 ELISA in samples from vehicle treated rats at termination (controls) as well as in $CCl_4$ treated rats at termination ($CCl_4$) at week 8, 12, 16, and 20. Results shown are mean±standard error of the mean (SEM). FIG. 4B: Serum levels of PIIINP using the PRO-C3 ELISA in samples from vehicle treated rats and $CCl_4$ rats stratified in quartiles according to total collagen in the liver. FIGS. 4C-4D: Correlation between PIIINP measured by PRO-C3

ELISA and Sirius red in samples from $CCl_4$ treated rats and in vehicle rats. Asterisks indicate statistical significance as indicated by bars. (*=p<0.05; =p<0.01; *=p<0.001, ns=non-significant difference).

Figure 5:
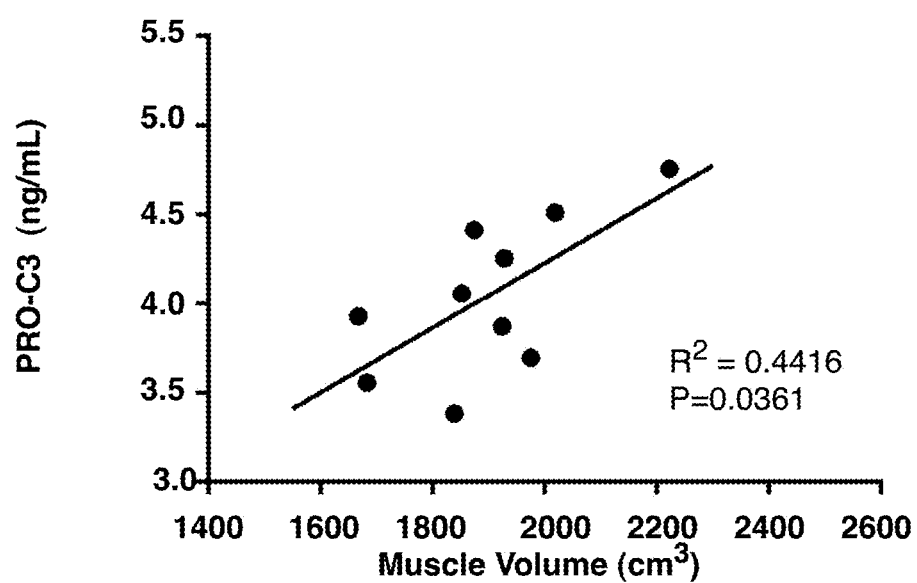

FIG. 5: Serum PIIINP titers measured in the PRO-C3 ELISA at baseline correlate significantly with quad muscle mass measured by thigh MRI using Pearson correlation. Data have not been transformed.

Figure 6:
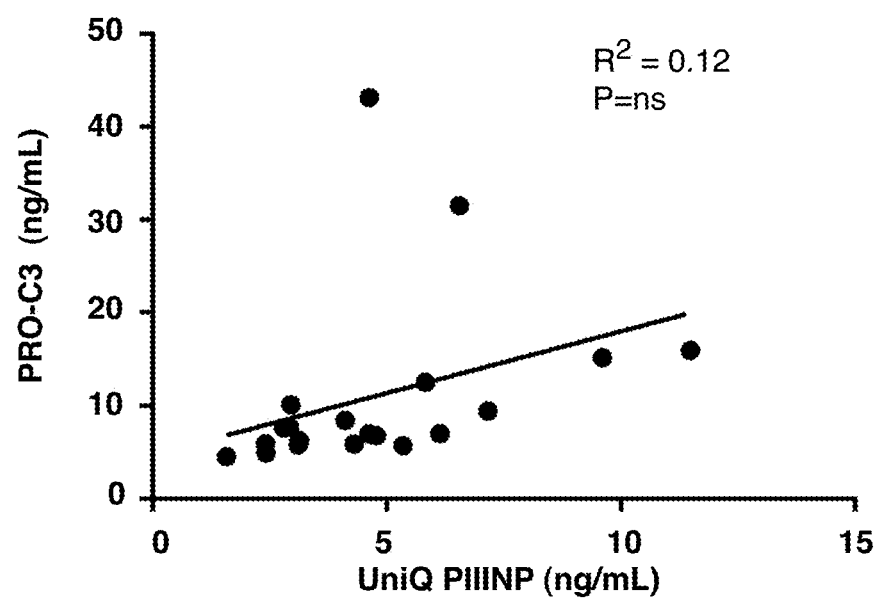

FIG. 6: Comparison between PIIINP measured in the PRO-C3 ELISA and UniQ PIIINP serum levels in 20 randomly selected serum samples from healthy human individuals; ns=non-significant difference.

Figure 7:
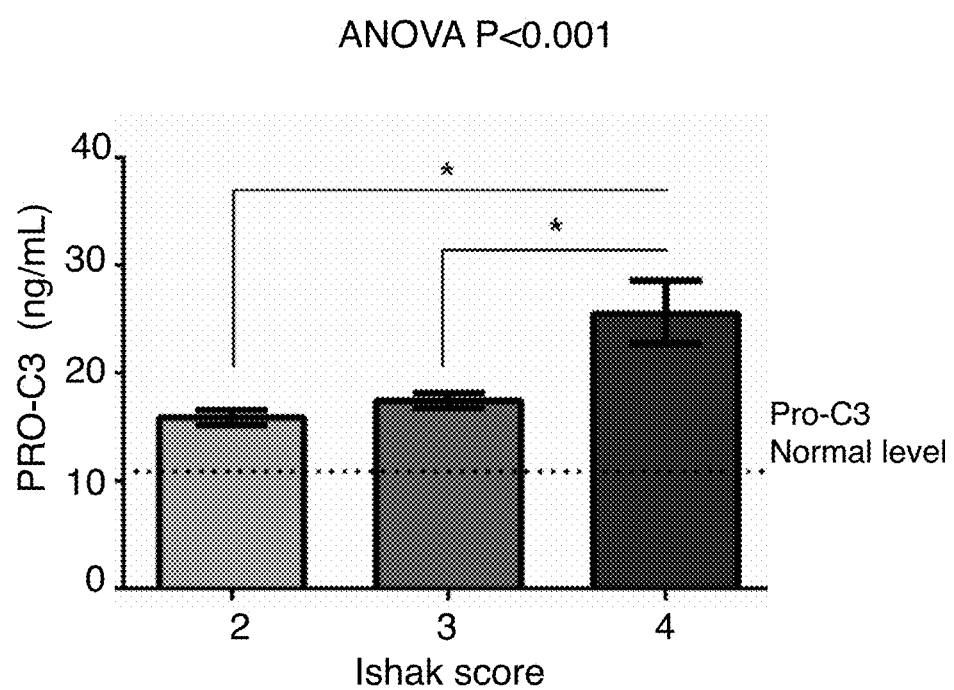

FIG. 7: Baseline levels of Plasma PIIINP in CHC patients stratified by Ishak stage. Pro-C3: Controls: 10.9 ng/mL (n=22); Ishak stage 2: 15.8 ng/mL (n=78); Ishak stage 3: 17.4 ng/mL (n=88) and Ishak stage 4: 25.5 ng/mL (n=28). The dotted horizontal line represents the level of controls. Data are presented as geometric mean±standard error of the mean (SEM). Asterisks indicate statistical significance indicated by bars: *p<0.05.

Figure 8A:
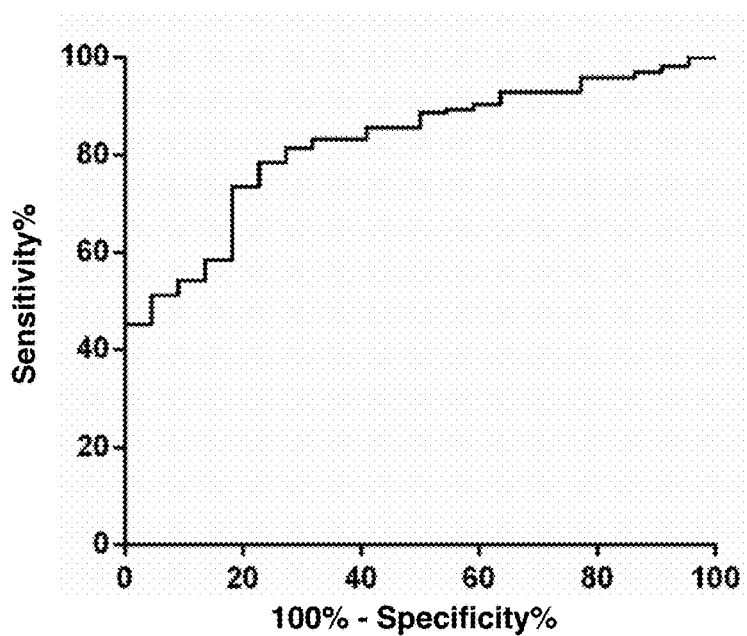
Figure 8B:
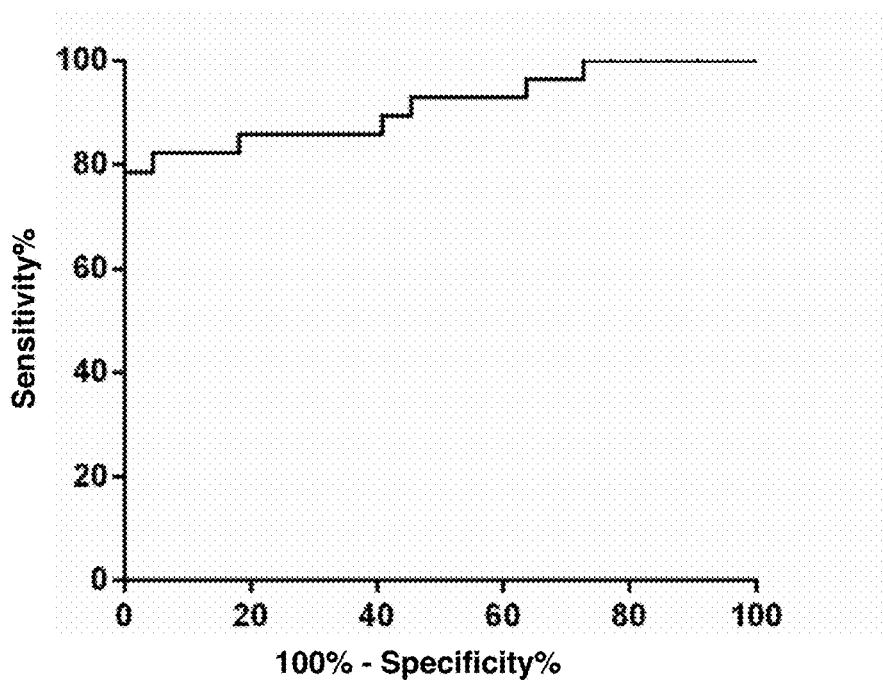
Figure 8C:
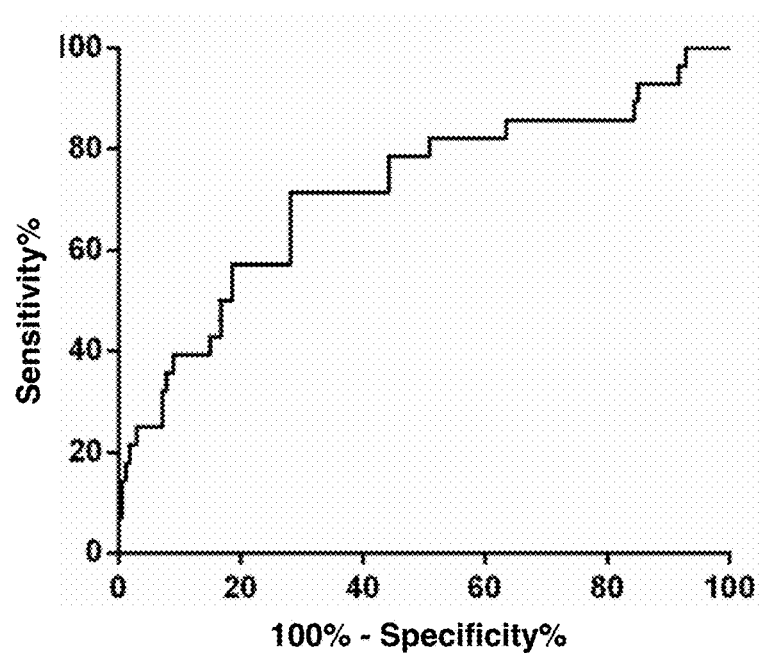
Figure 8D:
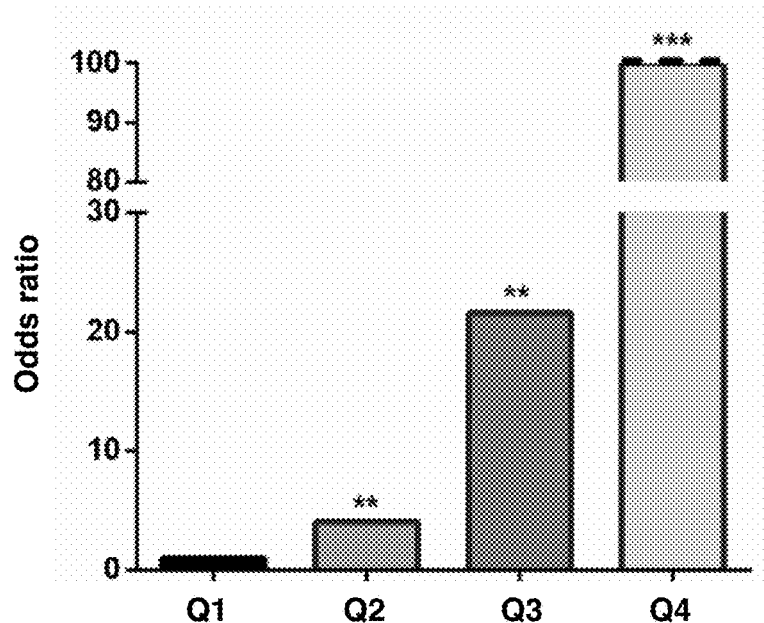

FIGS. 8A-8D: Diagnostic performance of Pro-C3. FIG. 8A: Receiver operating characteristic curve (ROC) analysis comparing controls (n=22) and mild fibrosis patients (Ishak stage 2 and 3, n=167). FIG. 8B: ROC analysis comparing controls (n=22) and moderate fibrosis patients (Ishak stage 4, n=28). FIG. 8C: ROC analysis comparing patients with mild fibrosis (n=167) and moderate fibrosis (n=28). FIG. 8D: Odds ratio for selecting CHC patients. Patients and controls (n=222) were divided into quartiles according to Pro-C3 plasma level. The broken top-line in Q4 represents a value above 100. Asterisks indicate statistical significance compared to Q1: p<0.001; *p<0.0001.

Figure 9:
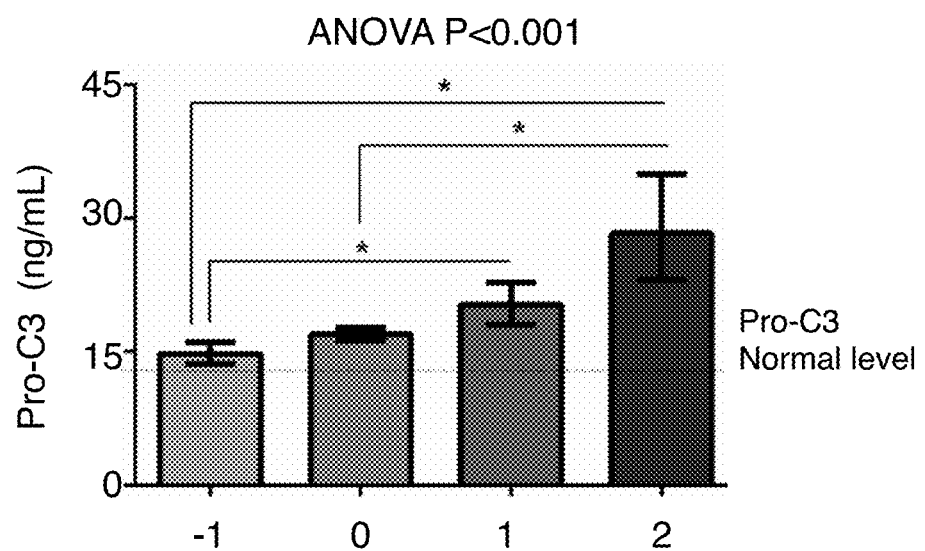

FIG. 9: Baseline levels of Plasma Pro-C3 in CHC patients stratified according to changes in Ishak stage after 52 weeks. Group −1: decrease of 1 in Ishak stage; Group 0: no change in Ishak stage; Group 1: increase of 1 in Ishak stage; and Group 2: increase of 2 Ishak stages. There is a significant increase in Pro-C3 in patients in Group 1 compared to Group −1, and in patients in Group 2 compared to both Group 0 and Group −1. Data are shown as geometric mean±SEM. Asterisks indicate statistical significance indicated by bars: *p<0.05.

Figure 10A:
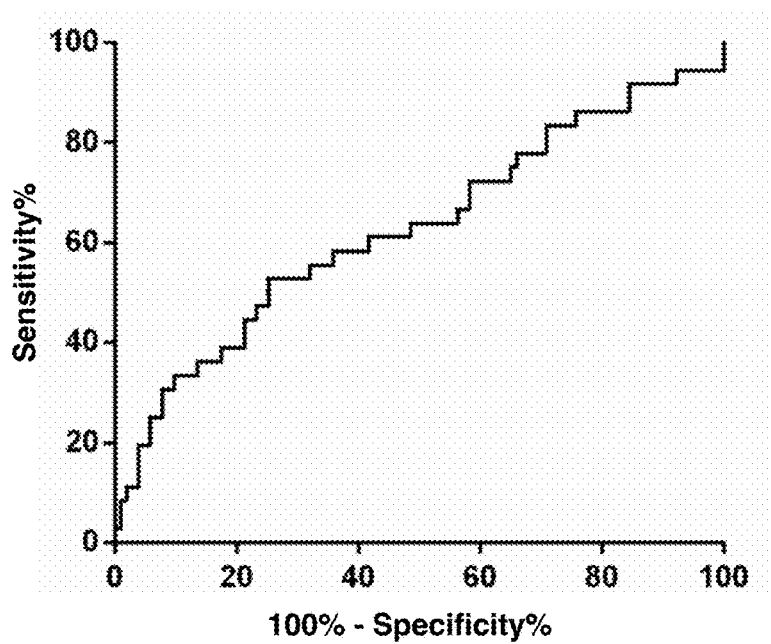
Figure 10B:
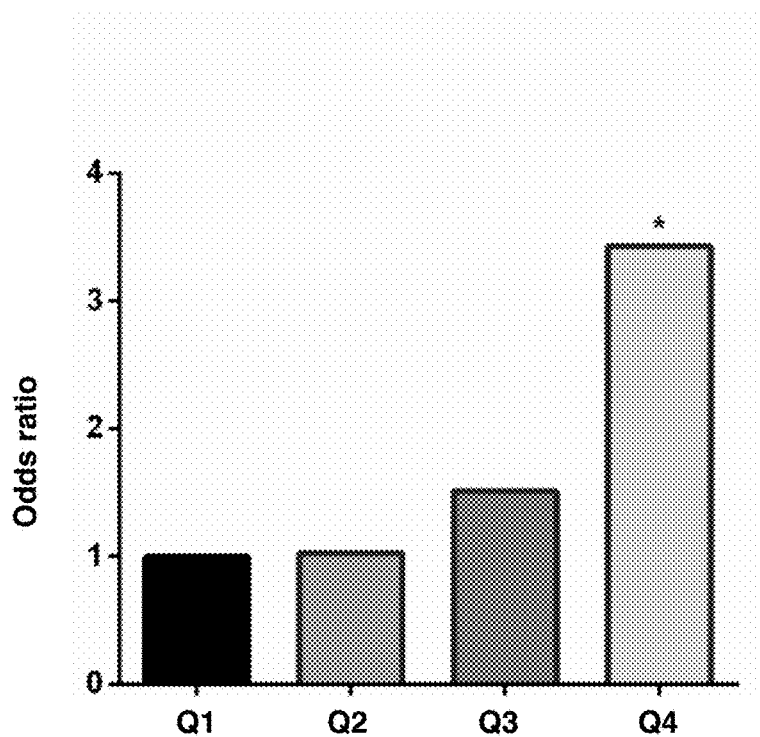

FIGS. 10A-10B: Prognostic performance of Pro-C3. FIG. 10A: ROC analysis comparing stable (n=103) and progressing fibrosis patients (n=36) yielded an AUC of 0.63 (p=0.023). FIG. 10B: Odds ratio of disease progression. Stable and progressing patients (n=139) were assigned into quartiles according to Pro-C3 plasma level. Q4 was associated with significant OR for disease progression (p=0.015), indicated by asterisk.

Figure 11:
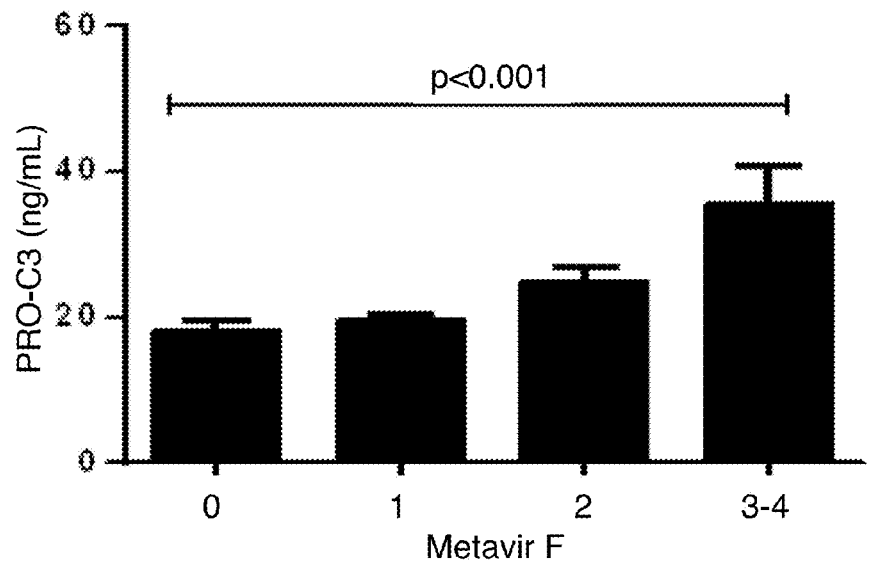

FIG. 11: Concentration of PRO-C3 (geometric mean with SEM) in Hepatitis B Virus (HBV) patients classified according to Metavir score.

Figure 12:
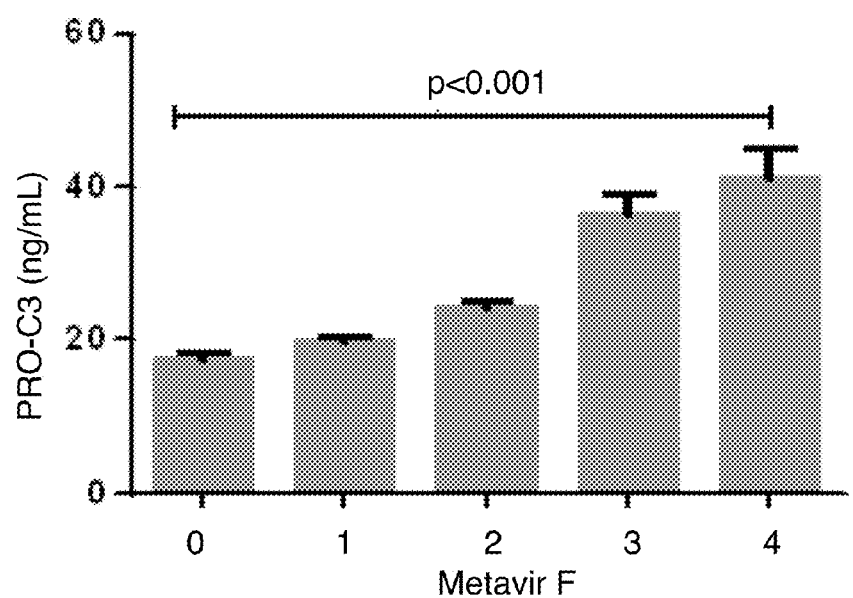

FIG. 12: Concentration of PRO-C3 (geometric mean with SEM) in Hepatitis C Virus (HCV) patients classified according to Metavir score.

Figure 13:
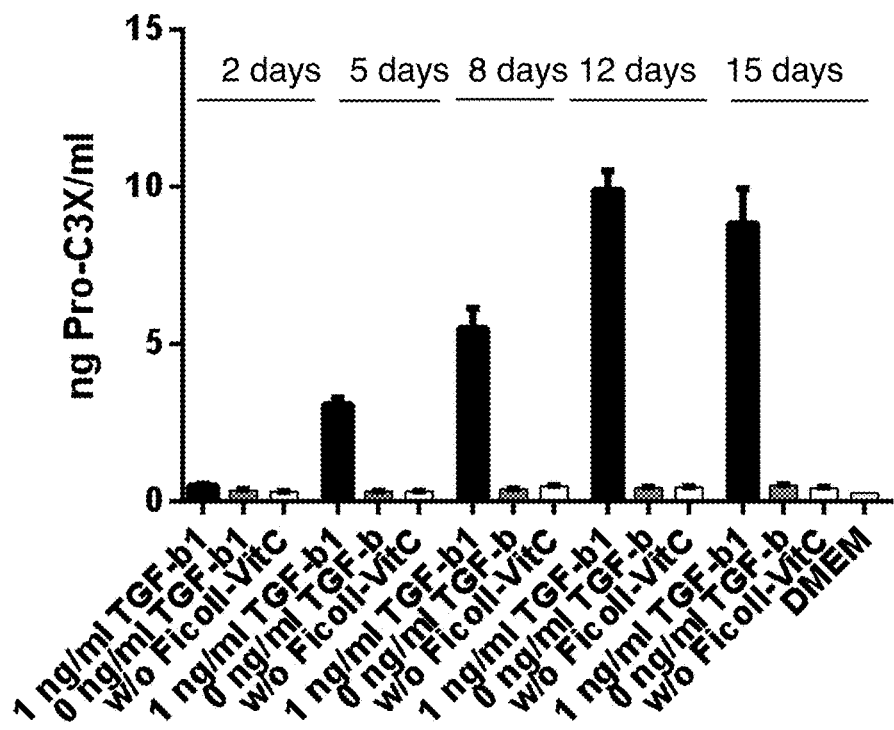

FIG. 13: Results of an in vitro model of lung fibroblasts ("scar-in-a-jar").

Figure 14:
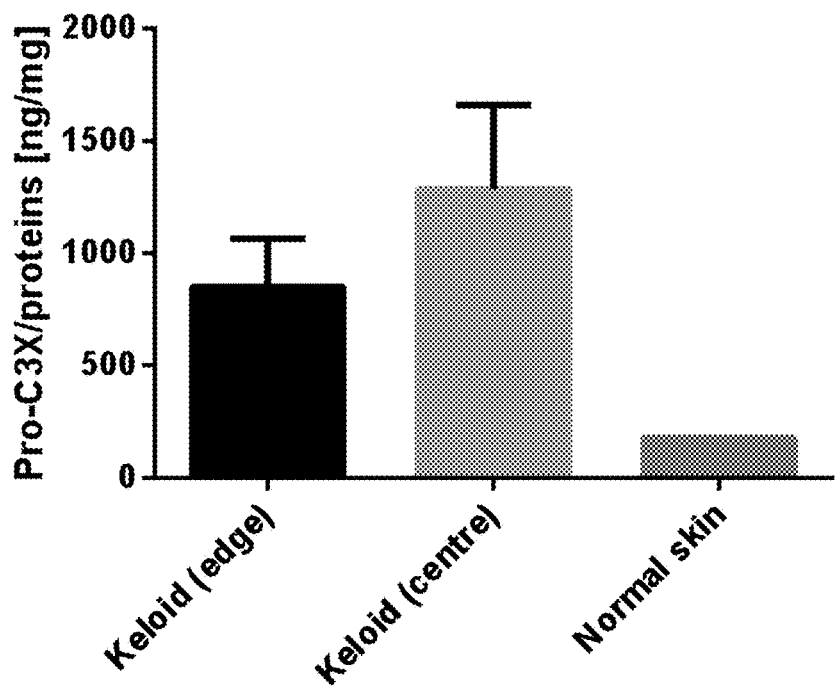

FIG. 14: A comparison of Pro-C3X levels in extractions from keloids and extractions from normal skin.

Figure 15A:
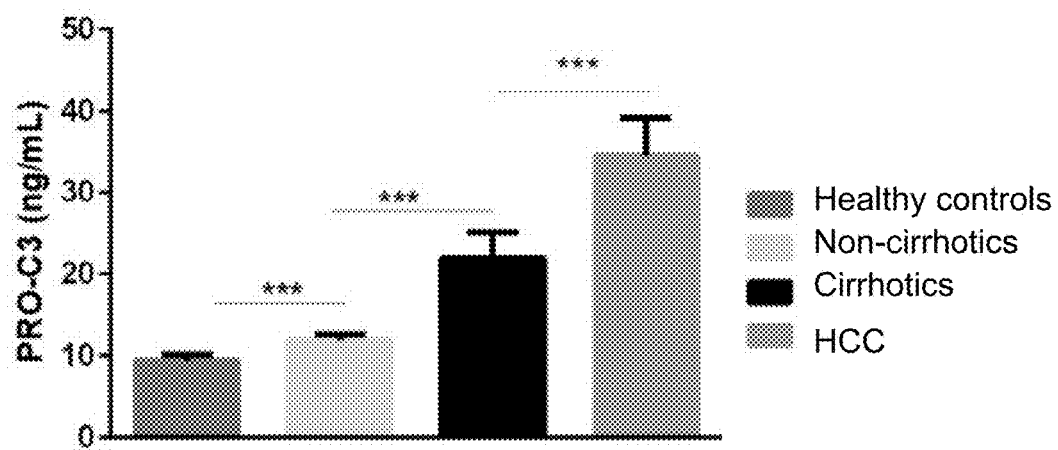
Figure 15B:
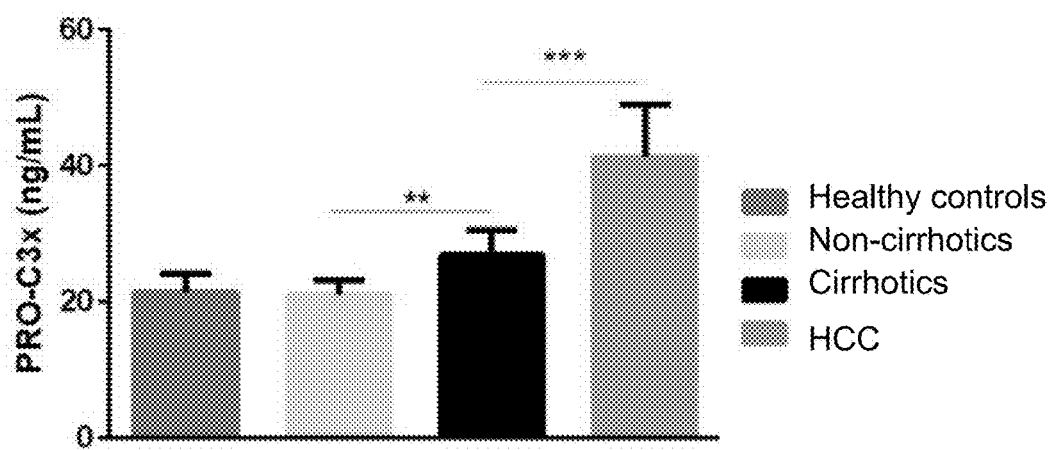

FIGS. 15A-15B: Results of a study of patients with liver fibrosis.

Figure 16:
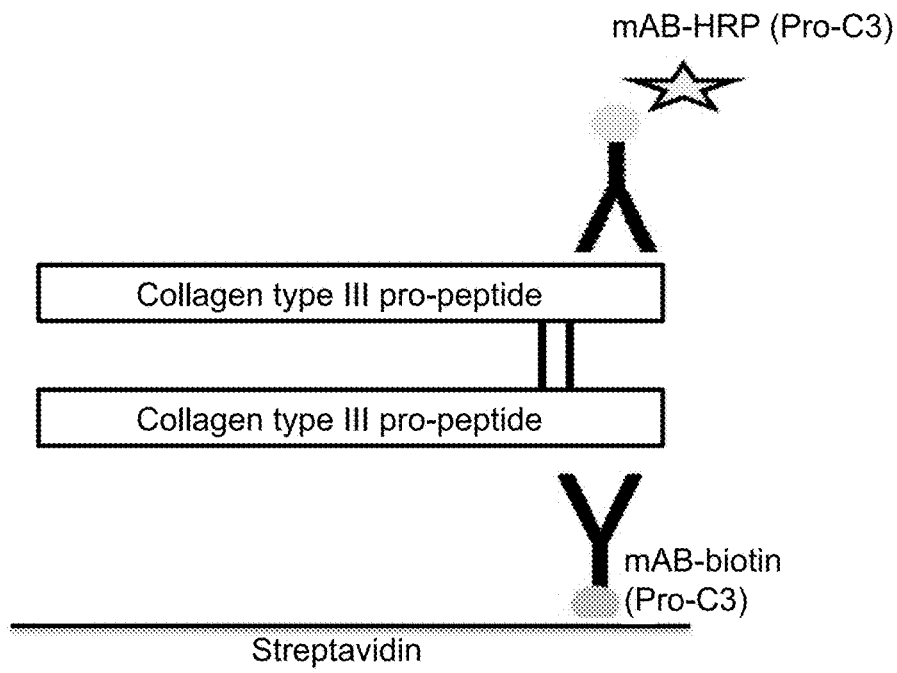

FIG. 16: Pictorial representation of the Pro-C3X assay.

Figure 17:
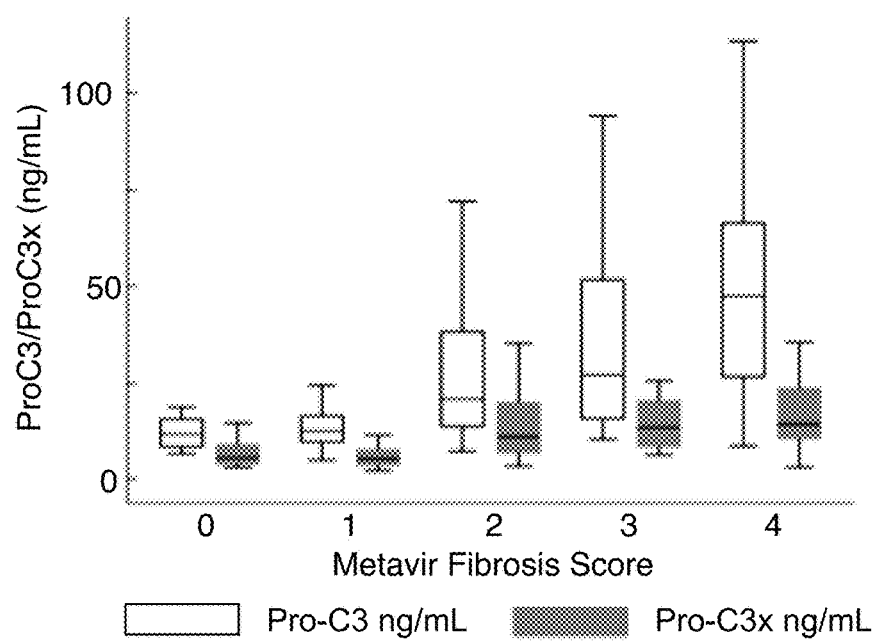

FIG. 17: Results of a study of patients with Alcoholic steatohepatitis.

DESCRIPTION OF THE INVENTION

As used herein the term "neo-epitope" refers to an N- or C-terminal peptide sequence at the extremity of a polypeptide, i.e. at the N- or C-terminal end of the of the polypeptide, and is not to be construed as meaning in the general direction thereof.

As used herein the term, the term "competitive ELISA" refers to a competitive enzyme-linked immunosorbent assay and is a technique known to the person skilled in the art.

As used herein the term, the monoclonal antibody NB61N-62 refers to a neo-epitope specific antibody directed towards the C-terminal neo-epitope of PIIINP, said neo-epitope comprising the C-terminal sequence CPTGXQ-NYSP-COOH (SEQ ID NO: 4), wherein X is Gly or Pro.

As used herein the term, the term "PRO-C3" is used to distinguish the herein described PIIINP assay from the PIIINP assays known in the art which are not based on the specific binding of neo-epitopes originating from PIIINP.

In a first aspect, the invention relates to a monoclonal antibody, wherein said monoclonal antibody is specifically reactive with a C-terminal neo-epitope of PIIINP, said neo-epitope being comprised in a C-terminal amino acid sequence CPTGXQNYSP-COOH (SEQ ID NO:4), wherein X is Gly or Pro, and wherein said monoclonal antibody does not substantially recognise or bind an elongated version of said C-terminal amino acid sequence which is CPTGXQ-NYSPQZ-COOH (SEQ ID NO: 5), wherein Z is absent or is one or more amino acids of the sequence of collagen type III.

In a preferred embodiment of the invention, the monoclonal antibody is specifically reactive with the neo-epitope C-terminal sequence CPTGPQNYSP-COOH (SEQ ID NO: 6) in human PIIINP, which is formed by the N-protease cleavage of PIIINP from intact procollagen type III at the Pro-Gln bond between amino acids P153-Q154 in human PIIINP.

In another preferred embodiment of the invention, the monoclonal antibody is specifically reactive with the neo-epitope C-terminal sequence CPTGGQNYSP-COOH (SEQ ID NO: 7) in rodent PIIINP, which said neo-epitope is formed by the N-protease cleavage of PIIINP from intact procollagen type III at the Pro-Gln bond between amino acids P154-Q155 in rodent PIIINP.

In another preferred embodiment of the invention, the ratio of the affinity of the monoclonal antibody for amino acid sequence CPTGXQNYSP-COOH (SEQ ID NO: 4) to the affinity of said monoclonal antibody for elongated amino acid sequence CPTGXQNYSPQZ-COOH (SEQ ID NO: 5) is at least 10 to 1, preferably at least 100 to 1, more preferably at least 1,000 to 1, more preferably at least 10,000 to 1, more preferably at least 100,000 to 1, and most preferably at least 1,000,000 to 1.

In another preferred embodiment of the invention, the monoclonal antibody does not recognise or bind a shortened version of a C-terminal neo-epitope of PIIINP, said shortened neo-epitope having the amino acid sequence CPTGX-QNYS (SEQ ID NO: 8).

In another preferred embodiment of the invention, the ratio of the affinity of the monoclonal antibody for amino acid sequence CPTGXQNYSP-COOH (SEQ ID NO: 4) to the affinity of said monoclonal antibody for shortened amino acid sequence CPTGXQNYS-COON (SEQ ID NO: 8) is at least 10 to 1, preferably at least 100 to 1, more preferably at least 1,000 to 1, more preferably at least 10,000 to 1, more preferably at least 100,000 to 1, and most preferably at least 1,000,000 to 1.

In another aspect, the present invention relates to a method of immunoassay for detecting in a biological sample the C-terminal neo-epitope of PIIINP generated by N-protease cleavage of intact type III procollagen, said method comprising contacting said biological sample comprising said C-terminal neo-epitope of PIIINP with a monoclonal antibody as described herein, and determining the amount of binding of said antibody.

In a preferred embodiment of the invention, the method of immunoassay is used to quantify the amount of PIIINP cleaved from intact collagen type III in a biofluid, wherein said biofluid may be, but is not limited to, serum, plasma or amniotic fluid.

In another preferred embodiment of the invention, the method of immunoassay may be, but is not limited to, a competition assay or a sandwich assay.

In another preferred embodiment of the invention, the method of immunoassay may be, but is not limited to, a radioimmunoassay or an enzyme-linked immunosorbent assay.

In another preferred embodiment of the invention, the method of immunoassay may further comprise correlating the quantity of PIIINP cleaved from intact collagen type III determined by said method with standard fibrotic disease samples of known disease severity to evaluate the severity of a fibrotic disease.

In another preferred embodiment of the invention, the method of immunoassay may be used to evaluate the severity of liver fibrosis by correlating the quantity of PIIINP cleaved from intact collagen type III determined by said method with standard liver fibrosis samples of known disease severity.

In another preferred embodiment of the invention, the method of immunoassay may be used to evaluate muscle volume by correlating the quantity of PIIINP cleaved from intact collagen type III determined by said method with MRI-determined muscle volume. In another embodiment, the present invention relates to a method for selecting patients having a fibrotic disease which is in a deteriorating condition for pharmaceutical trial or therapy, wherein said method comprises determining the severity of said fibrotic disease, determining the quantity of PIIINP cleaved from intact collagen type III using an immunoassay as described herein, and selecting from a group of patients determined to have an equivalent severity of said fibrotic disease those patients having a quantity of PIIINP above a statistical second quartile, and preferably in a statistical upper quartile. The severity of the fibrotic disease may be determined using any suitable method, including, but not limited to, the Ishak fibrosis staging scale or METAVIR scoring.

In another aspect, the present invention provides an assay kit for determining the quantity of PIIINP in a biological sample, said assay kit comprising a monoclonal antibody as described herein and at least one of:
  a streptavidin coated 96 well plate;
  a biotinylated peptide Biotin-L-CPTGPQNYSP (SEQ ID NO: 9), wherein L is an optional linker;
  a biotinylated secondary antibody for use in a sandwich immunoassay;
  a calibrator peptide comprising the C-terminal sequence CPTGPQNYSP-COOH;
  an antibody HRP labeling kit;
  an antibody radiolabeling kit; and/or
  an assay visualization kit.

In another aspect, the present invention relates to a sandwich immunoassay for detecting in a biological sample cross-linked PIIINP, said cross-linked PIIINP comprising at least two strands of PIIINP joined together by inter-strand cross-linking, said method comprising:
  contacting said biological sample comprising said cross-linked PIIINP with a first monoclonal antibody bound to a surface, wherein each strand of PIIINP comprised in the cross-linked PIIINP comprises a C-terminal neo-epitope of PIIINP generated by N-protease cleavage of intact type III procollagen;
  adding a second monoclonal antibody; and
  determining the amount of binding of said second monoclonal antibody;
  wherein both said first monoclonal antibody and said second monoclonal antibody are specifically reactive with said C-terminal neo-epitope of PIIINP, said neo-epitope being comprised in a C-terminal amino acid sequence CPTGXQNYSP-COOH, wherein X is Gly or Pro.

Preferably, the monoclonal antibody does not substantially recognise or bind an elongated version of said C-terminal amino acid sequence which is CPTGXQNYSPQZ-COOH, wherein Z is absent or is one or more amino acids of the sequence of collagen type III.

The herein described sandwich immunoassay uses the same antibody as both catcher and detector antibody, therefore a double strand peptide (i.e. cross-linked) can be recognized by the assay.

Preferably, the sandwich immunoassay is used to quantify the amount of cross-linked PIIINP in a biofluid, wherein said biofluid may be, but is not limited to, serum, plasma, urine, amniotic fluid, tissue supernatant or cell supernatant.

The sandwich immunoassay may be, but is not limited to, a radioimmunoassay, fluorescence immunoassay, or an enzyme-linked immunosorbent assay.

In a preferred embodiment, the second monoclonal antibody may be labeled in order to determine the amount of binding of said second monoclonal antibody.

Preferably, the second monoclonal antibody may be an enzyme-linked antibody. The enzyme may be, but is not limited to, horseradish peroxidase (HRP). Preferably, the second monoclonal antibody may be radiolabeled or linked to a fluorophore.

Although these are preferred labels to be used with the invention, it is envisaged that any suitable labeling system may be employed, such as, but not limited to, DNA reporters or electrochemiluminescent tags.

Alternatively, a further labeled antibody which recognises the second monoclonal antibody may be used to determine the amount of binding of said second monoclonal antibody. The further labeled antibody may be labeled using a label as described above.

In a preferred embodiment of the invention, the sandwich immunoassay may further comprise correlating the quantity of cross-linked PIIINP determined by said method with standard fibrotic disease samples of known disease severity to evaluate the severity of a fibrotic disease. Such a fibrotic disease may be, but is not limited to, liver disease.

In a further aspect, the sandwich immunoassay described herein may be used in a method for evaluating the efficacy of a drug targeting lysyl oxidases (LOXs), such as an antagonist drug targeting LOXs.

Accordingly, the present invention also relates to a method for evaluating the efficacy of an antagonist drug targeting lysyl oxidases (LOXs), wherein said method comprises using the sandwich immunoassay described herein to quantify the amount of cross-linked PIIINP in at least two biological samples, said biological samples having been obtained from a subject at a first time point and at least one subsequent time point during a period of administration of the antagonist drug to said subject, and wherein a reduction in the quantity of cross-linked PIIINP from said first time point to said at least one subsequent time point during the period of administration of the antagonist drug is indicative of an efficacious antagonist drug targeting LOXs.

Preferably, the method quantifies the efficaciousness of the antagonist drug.

Preferably, the method evaluates the efficacy of an antagonist drug targeting LOXL2.

In another aspect, the present invention relates to a kit for use in the sandwich immunoassay as described herein, the kit comprising a solid support to which is bound a first monoclonal antibody as described above; and a labelled second monoclonal antibody as described above.

EXAMPLES

Materials and General Considerations

All reagents used in the experiments were high-standard chemicals from companies such as Merck (Whitehouse Station, N.J., USA) and Sigma Aldrich (St. Louis, Mo., USA). The synthetic peptides used for monoclonal antibody production and validation were 1) Immunogenic peptide: Ovalbumine (OVA)-CGG-CPTGPQNYSP (SEQ ID NO: 10), 2) Screening peptide: Biotin-CGG-CPTGPQNYSP (SEQ ID NO: 11), and 3) Selection peptide: CPTGPQNYSP (SEQ ID NO 6). All synthetic peptides were purchased from the Chinese Peptide Company, Beijing, China.

Example 1

Monoclonal Antibody NB61-N62

Monoclonal Antibody Generation

The sequence for the N-terminal propeptide of type III collagen was aligned between human, rat and mouse species and selected from homology between the species and uniqueness among other ECM proteins by protein blasting. The amino acid sequence 145'-CPTGPQNYSP-'153 (SEQ ID NO: 6) in the α1 chain PIIINP is 100% homologues between human and rat (FIG. 1). Generation of monoclonal antibodies was initiated by subcutaneous immunization of 4-5 week old Balb/C mice with 200 µl emulsified antigen and 50 µg PIIINP neo-epitope C-terminal sequence (OVA-CGG-CPTGPQNYSP (SEQ ID NO: 10)) using Freund's incomplete adjuvant. The immunizations were repeated every 2 weeks until stable serum titer levels were reached. The mouse with the highest serum titer was selected for fusion. The mouse was rested for a month and then boosted intravenously with 50 µg PIIINP neo-epitope C-terminal sequence in 100 µl 0.9% NaCl solution three days before isolation of the spleen. The spleen cells were fused with SP2/0 myeloma cells to produce hybridoma as described by (34), and cloned in culture dishes using the semi-medium method. The clones were plated into 96-well microtiter plates for further growth employing the limited dilution method to secure monoclonal growth. The supernatants were screened for reactivity against calibrator peptide and native material in an indirect ELISA using streptavidin-coated plates. Biotin-CGG-CPTGPQNYSP (SEQ ID NO: 11) was used as screening peptide, while the free peptide CPTGPQNYSP (SEQ ID NO: 6) was used as calibrator to test for further specificity of clones.

Clone Characterization

Native reactivity and affinity of the peptide were assessed using different biological materials such as urine, serum, and amniotic fluid (AF) from both humans and rats in a preliminary ELISA using 2 ng/ml biotinylated peptide on streptavidin-coated microtiter plates and the supernatants from growing monoclonal hybridoma cells. Human AF was obtained from 30 women undergoing elective lower segment Caesarean sections at the Beijing Obstetrics Gynecology Hospital over a 2 month period. 100-200 ml AF was collected directly after incision and the fluid was stored at $-20°$ C. until use. The local ethical board had approved the study and all women provided written consent prior to collection. Rat AF was drawn from the uterus of pregnant Wistar rats two days prior to expected birth. Antibody specificity was tested in a preliminary assay using deselection and elongated peptides (i.e. calibrator peptide with ten amino acid substitutions and calibrator peptide with one additional amino acid at the cleavage site, respectively). The isotype of the monoclonal antibodies was determined using the Clonotyping System-HRP kit, cat. 5300-05 (Southern Biotech, Birmingham, Ala., USA).

Antibody Characterization

Prior to Western Blotting, the total protein concentration of human and rat AF was measured using Bicinchoninic acid (BCA) Protein Assay according to manufacturer's instruction. Briefly, BCA was diluted 2-fold in PBS from 2 mg/ml to produce a standard row for calculation of the samples. Samples were diluted 1:4 in 1× phosphate-buffered saline (PBS) and 25 µl sample was added to a microtiter plate along with 200 µl working reagent (Reagent A and B mixed in the ratio 50:1). The content was mixed on a plate shaker for 30 seconds followed by incubation for 30 minutes at 37° C. After ended incubation the plate was cooled to room temperature and the absorbance was measured in the ELISA reader at 562 nm (Molecular Devices, SpectraMax M, CA, USA). Hereafter, rat or human AF was mixed with sample buffer (×2) and reducing agent (×10), heated at 70° C. for 10 minutes, loaded on a 4-20% tris-glycein sodium dodecyl sulphate-polyacrylamide gel electrophoresis (SDS-page), and run for 1 hour at 180V. Protein bands were blotted onto a nitrocellulose membrane using the Invitrogen i-Blot gel transfer system according to manufacturer's instruction. The membrane was blocked in blocking buffer (5% skimmed milk in Tris-buffered saline with Tween (TBST) overnight at 4° C. and incubated with 1 µg/ml horseradish peroxidase (HRP)-conjugated PIIINP neo-epitope specific monoclonal antibody NB61N-62 for 2 hours. Specificity of the PIIINP neo-epitope specific monoclonal antibody was investigated by addition of excess PIIINP neo-epitope calibrator peptide and antibody in the ratio 10:1 and allowed to pre-incubate for 1 hour before it was added to the membrane for overnight incubation. After incubation the membranes was washed 4×10 minutes in TBST, incubated with 4 ml chemiluminescence detection kit (ECL), and developed using Amersham Hyperfilm.

Clone Selection and Characterization

The subtype was determined to be an IgG1 subtype. From the Western Blot analysis it was seen that the PIIINP neo-epitope specific monoclonal antibody NB61N-62 recognized two bands with molecular sizes around 52-60 kDa in rat amniotic fluid, while only one band around 52 kDa was detected in human amniotic fluid. In addition, the signal could be partly inhibited by the selection peptide in the rat, and inhibited in human (FIG. 2). Native reactivity was observed using the NB61N-62 antibody in the ELISA. Native reactivity was seen towards human serum, plasma, and AF as well as against rodent serum, plasma, and AF (FIGS. 3A-3C). The signal was slightly less inhibited against mouse serum and plasma. The signal of the competitive ELISA was inhibited using from 1:2 to 1:16, undiluted to 1:8, or undiluted to 1:4 in human, rodent, and mouse native material, respectively. Dilution of the native material approximately followed the same dilution pattern as the calibrator curve for all three species. Human AF inhibited the signal up to 100%; 80% for rat AF; 70% for human serum and plasma and rat serum; 44% for rat plasma, and 35% for mouse serum and plasma. Zero inhibition was observed using the elongated peptide (CPTGPQNYSPQ (SEQ ID NO: 6)) and non-sense peptide (GSPGKDGVRG (SEQ ID NO: 12)) (FIG. 3D).

Example 2

PRO-C3 ELISA Using NB61N-62

Supernatant from the antibody producing hybridoma was collected and the monoclonal antibody was purified using HiTrap affinity columns (GE Healthcare Life Science, Little Chalfont, Buckinghamshire, UK) and labeled with HRP using Lightning-Link™ HRP Conjugation Kit (Innova Biosciences, Babraham, Cambridge, UK), according to the manufacturer's instructions.

The PRO-C3 competitive ELISA procedure was as follows: A 96-well streptavidin-coated ELISA plate from Roche, cat.11940279, was coated with the biotinylated peptide Biotin-CGG-CPTGPQNYSP (SEQ ID NO: 11) dissolved in coater buffer (50 mM PBS-BTE+10% sorbitol, pH 7.4), incubated for 30 min at 20° C. in the dark and subsequently washed in washing buffer (20 mM Tris, 50 mM NaCl, pH 7.2). Thereafter 20 µl of peptide calibrator or sample were added to appropriate wells, followed by 100 µl of HRP-conjugated monoclonal antibody NB61N-62 dissolved in incubation buffer (50 mM PBS-BTB+10% LiquidII (Roche), pH 7.4) and the plate was incubated for 20 hours at 4° C. and washed. Finally, 100 µl tetramethylbenzinidine (TMB) (Kem-En-Tec cat.: 4380H) was added, the plate was incubated for 15 min at 20° C. in the dark and in order to stop the reaction, 100 µl of stopping solution (1% $H_2SO_4$) was added and the plate was analyzed in the ELISA reader at 450 nm with 650 nm as the reference (Molecular Devices, SpectraMax M, CA, USA). A calibration curve was plotted using a 4-parametric mathematical fit model.

Technical Evaluation

A 2-fold dilution of healthy serum and plasma samples from human and rats were used to determine linearity and calculated as percentage of recovery of the 100% sample. Antibody specificity was calculated as percentage of recovery of the 100% calibrator peptide (CPTGPQNYSP (SEQ ID NO: 6)), elongated peptide (CPTGPQNYSPQ (SEQ ID NO: 13)), and non-sense peptide (GSPGKDGVRG (SEQ ID NO: 12)). Lower limit of detection (LLOD) was calculated as the mean+3×Standard Deviation (SD) of the blank from 21 determinations of standard K (i.e. buffer). Upper limit of detection (ULOD) was determined as the mean−3×SD of 10 measurements of Standard A. Lower limit of quantification (LLOQ) was determined as the lowest concentration reproducibly measured with a precision lower than 30%. The intra- and inter-assay variation was determined by 10 independent runs of 8 QC samples, with each run consisting of double determination of the samples. Accuracy of the samples was measured in healthy human serum samples spiked with standard curve or human amniotic fluid at significant concentrations and calculated as the percentage recovery of the theoretical amount of serum. Interference was measured in healthy human serum spiked with hemoglobin, lipemia, and biotin at significant concentrations and calculated as the percentage recovery of the theoretical amount of serum.

Results

The measurement range of the human PRO-C3 ELISA was determined by calculating ULOD and LLOQ providing a range from 0.867-60.1 ng/ml with a LLOD of 0.606 ng/ml. The technical performance of the PRO-C3 ELISA showed acceptable inter- and intra assay variation of mean 11.03% and 4.11% (Table 1), with acceptance range below 15% and 10%, respectively.

TABLE 1

Inter- and intra-assay variation for the PRO-C3 assay using human serum quality control samples # 1-8 (HS1-HS8). The variation was calculated as the mean variation between 10 individual determinations of each sample.

| Sample | Value (ng/mL) | Intra-assay variability % | Inter-assay variability % |
|---|---|---|---|
| HS1 | 24.24 | 2.28 | 5.94 |
| HS2 | 11.62 | 2.90 | 6.45 |
| HS3 | 8.40 | 5.31 | 11.99 |
| HS4 | 6.54 | 4.46 | 11.31 |
| HS5 | 6.36 | 3.88 | 13.09 |
| HS6 | 5.23 | 3.98 | 12.31 |
| HS7 | 4.29 | 3.53 | 12.94 |
| HS8 | 2.98 | 4.66 | 18.56 |

Dilution recovery was performed using healthy serum and plasma samples from humans, rat and mouse. The dilution recovery was within the acceptable 100±20% recovery (Table 2). Further dilution resulted in measurements below LLOQ.

TABLE 2

Percentage dilution recovery for the PRO-C3 assay using human-, rat-, and mouse samples. Human serum (HS), Human plasma (HP), Rat serum (RS), Mouse serum (MS), Mouse plasma (MP).

| PIIINP ng/ml | HS (n = 2) | HP (n = 3) | RS (n = 10) | MS (n = 2) | MP (n = 2) |
|---|---|---|---|---|---|
| Undiluted | 100% | — | 100% | 100% | — |
| Dilution 1:2 | 98 | 100% | 116 | 96 | 100% |
| Dilution 1:4 | 103 | 91 | 110 | 118 | 114 |
| Dilution 1:8 | 114 | 87 | — | — | — |
| Dilution 1:16 | — | 92 | — | — | — |
| Mean | 105 | 90 | 113 | 107 | 114 |

Spiking of calibrator peptide in serum or plasma resulted in a mean recovery of 56% and 55%, respectively (Table 3).

TABLE 3

Spiking recovery of calibrator peptide in human serum or plasma, and human AF in human serum or plasma. The recovery was calculated as percent recovery of calculated peptide/AF in serum/plasma compared to pure serum/plasma. Concentration of calibrator peptide were 38.16 ng/ml (StdB), 19.08 ng/ml (StdC), 9.54 ng/ml (StdD), 4.77 ng/ml (StdE), 2.39 ng/ml (StdF) and 1.19 ng/ml (StdG). AF wasadded in 2-fold dilution starting from 1:2.

| Added Std | Serum (n = 3) sRE % | Plasma (n = 3) sRE % | Added AF | Serum (n = 3) sRE % | Plasma (n = 3) sRE % |
|---|---|---|---|---|---|
| StdB | 16 | 15 | 2x | 101 | 103 |
| StdC | 29 | 25 | 4x | 103 | 108 |
| StdD | 42 | 38 | 8x | 106 | 113 |
| StdE | 58 | 54 | 16x | 103 | 112 |

TABLE 3-continued

Spiking recovery of calibrator peptide in human serum or plasma, and human AF in human serum or plasma. The recovery was calculated as percent recovery of calculated peptide/AF in serum/plasma compared to pure serum/plasma. Concentration of calibrator peptide were 38.16 ng/ml (StdB), 19.08 ng/ml (StdC), 9.54 ng/ml (StdD), 4.77 ng/ml (StdE), 2.39 ng/ml (StdF) and 1.19 ng/ml (StdG). AF wasadded in 2-fold dilution starting from 1:2.

| Added Std | Serum (n = 3) sRE % | Plasma (n = 3) sRE % | Added AF | Serum (n = 3) sRE % | Plasma (n = 3) sRE % |
|---|---|---|---|---|---|
| StdF | 70 | 69 | 32x | 104 | 115 |
| StdG | 82 | 83 | 64x | 103 | 110 |
| Buffer | 92 | 100 | Buffer | 99 | 104 |
| Mean sRE % | 56 | 100 | Mean sRE % | 55 | 111 |

However, spiking of human AF in 2-fold dilution starting from 1:2 into healthy human serum or plasma resulted in mean recovery of 100% and 111%, respectively. No interference was observed in serum spiked with different concentrations of hemoglobin, biotin, and lipemia (Table 4).

TABLE 4

Interference of hemoglobin, lipemia and biotin in human serum added in various concentrations. All data are shown as percent recovery compared to pure serum.

| Hemoglobin | | Lipemia | | Biotin | |
|---|---|---|---|---|---|
| mmol/L | RE % | mmol/L | RE % | ng/L | RE % |
| 0.5 | 68 | 0.56 | 101 | 160,000 | 134 |
| 0.25 | 74 | 0.28 | 103 | 80,000 | 113 |
| 0.13 | 81 | 0.14 | 99 | 40,000 | 96 |
| 0.063 | 81 | 0.07 | 104 | 20,000 | 97 |
| 0.031 | 82 | 0.04 | 101 | 10,000 | 94 |
| 0.016 | 86 | 0.00 | 100 | 5,000 | 87 |
| 0.008 | 95 | | | 2,500 | 100 |
| 0.000 | 100 | | | 0 | 100 |
| Mean | 83 | | 101 | | 103 |

The stability of the analyte was acceptable up to four freeze/thaw cycles with 100±20% recovery compared to 1 freeze/thaw cycle (Table 5).

TABLE 5

Analyte stability in three human serum and plasma samples in four freeze/thaw cycles. All data are shown as mean percent recovery compared to 1 freeze/thaw cycle.

| Freeze/thaw cycle | Serum Mean recovery % | EDTA plasma Mean recovery % | Heparin plasma Mean recovery % | Citrate plasma Mean recovery % |
|---|---|---|---|---|
| 1 | 100% | 100% | 100% | 100% |
| 2 | 103 | 102 | 103 | 109 |
| 3 | 99 | 99 | 98 | 103 |
| 4 | 102 | 100 | 98 | 100 |

Example 3

Determining the Ratio of Binding Affinity

To determine the ratio of the binding affinity of the monoclonal antibody for the target sequence to the binding affinity of the monoclonal antibody for the elongated or shortened sequence, each of the sequences are synthesized and used as calibrator peptides in the PRO-C3 ELISA as described in example 2. The resultant calibration curves are used to determine the $IC_{50}$ values of each sequence/antibody combination. The ratio of $IC_{50}$[target]/$IC_{50}$[elongated or shortened] defines the ratio of binding affinity.

Example 4

Rat $CCl_4$ Liver Fibrosis Model

Serum levels of PIIINP were assessed in a $CCl_4$ inhalation rat model of liver fibrosis. Complete details of the study are described elsewhere (35). The study included 52 male Wistar rats treated with $CCl_4$ and 28 male Wistar vehicle rats (Charles-River, Saint Aubin les Elseuf, France). Induction of liver fibrosis was performed as previously described by others (36). Briefly, $CCl_4$ was administered by inhalation twice a week, starting with 0.5 minutes per exposure. The duration of exposure was increased by one minute after every three session until it reached five minutes, which was used until the end of the investigation. Phenobarbital (0.3 g/l) was added to the drinking water and vehicle rats received phenobarbital only. Animals were stratified into groups receiving 8, 12, 16, or 20 weeks of $CCl_4$ or vehicle treatment (n=13 for $CCl_4$; n=7 vehicle for each group). The study was performed according to the criteria of the Investigation and Ethics Committee of the Hospital Clinic Universitari (Barcelona, Spain), approval #B-NNP-233/09. Four animals from the $CCl_4$ groups died during the study. Blood was collected at termination and allowed to stand at room temperature for 20 min to clot before centrifugation at 2500 rpm for ten minutes. Samples were stored at −80° C. prior to biomarker assessment in the PRO-C3 ELISA.

Results

Serum levels of PIIINP determined in the PRO-C3 ELISA were statistically elevated in $CCl_4$ treated rats compared to vehicle rats at week 8 (+30.17% increase, $p<0.001$), week 12 (+26.58% increase, $p<0.05$), and week 16 (+44.15% increase, $p<0.05$), however not in week 20 (+6.24% increase, p=ns) (FIG. 4A). When rats were stratified into quartiles according to total amount of collagen in the liver assessed by Sirius Red staining, PIIINP was statistically elevated in all four quartiles compared to vehicle animals (quartile 1 (Q1)+21% increase, $p<0.01$; Q2+21% increase, $p<0.05$; Q3+33% increase, $p<0.001$; Q4+56% increase, $p<0.001$) (FIG. 4B). Furthermore, serum levels of PIIINP were correlated to the total collagen in the liver. PIIINP correlated significantly to collagen in $CCl_4$ rats (r=0.46, $p<0.01$), however not in vehicle rats (r=0.07, p=ns) (FIGS. 4C-4D).

During liver fibrosis the amount of ECM components are known to be highly increased, up to 6 fold (37), including type III collagen, and it is well known that PIIINP is a marker for describing liver fibrosis (34,35,36,37). The PRO-C3 ELISA described herein was used to evaluate the quantity of PIIINP in a rat model of liver fibrosis. It was found that serum PIIINP was significantly elevated at termination after 8, 12 and 16 weeks and when stratified into quartiles of the total amount of collagen compared to controls. At the 20 week termination point serum PIIINP had regressed back to control levels. These data indicate that this marker reflects fibrogenesis rather than degradation since the serum PIIINP determined by the PRO-C3 ELISA were initially high in this model.

Example 5

Muscle Loss

PIIINP was measured by PRO-C3 ELISA in plasma samples from 11 young men (n=11, age: 24.4±0.5 y, height: 181.4±1.8 cm, weight: 72.2±2.3 kg) that were subjected to two weeks of unilateral leg immobilization (through full leg casting) followed by four weeks of resistance training remobilization. Subjects were sampled for venous blood, leg muscle volume and strength at baseline (PRE), after immobilization (2W) and after remobilization (4W). During immobilization the subjects lost approximately 9 and 20%, of muscle size (MRI-determined quadriceps muscle volume) and strength (knee extensor force measured by maximal voluntary contraction in KinCom device) respectively, as previous reported (38). Subjects were not fasted or placed on custom diets prior to testing and sampling. Samples were stored at −80° C. prior to biomarker assessment in the PRO-C3 ELISA.

Results

Levels of PIIINP did not differ significantly between intervention time points when correlated against muscle mass at baseline, however a significant positive correlation was observed between PIIINP and muscle volume ($R^2=0.4416$, $P=0.0361$) (FIG. 5), meaning that higher PIIINP levels strongly predict higher muscle mass in healthy individuals not exposed to any intervention.

Example 6

Comparison of Competitive PRO-C3 ELISA and UniQ PIIINP Assays 20 randomly selected healthy human serum samples were evaluated for PIIINP using the competitive PRO-C3 ELISA and the results compared with the results obtained by measuring the level of PIIINP using the UniQ PIIINP RIA (Orion Diagnostica, Espoo, Finland) according to the manufacturer's instructions.

Results

Serum levels of PIIINP as determined by the competitive PRO-C3 ELISA did not correlate significantly to serum levels of PIIINP as determined by the UniQ PIIINP RIA ($R^2=0.12$, p=ns) (FIG. 6). The competitive PRO-C3 ELISA described herein quantifies the formation of type III collagen and not degradation. The lack of correlation between the results from said competitive PRO-C3 ELISA and the UniQ PIIINP RIA is further evidence that the commercially available immunoassays for PIIINP detection and/or quantification do not differentiate between PIIINP formed by collagen type III formation and PIIINP formed by collagen type III degradation.

Example 7

PIIINP Assessments in Plasma Samples from Patients with Chronic Hepatitis C (CHC)

The study cohort was from a multicenter, phase II clinical study to assess the effectiveness of farglitizar, a peroxisome proliferator-activated receptor-gamma agonist, as a potential antifibrotic compound for adult CHC patients (NCT00244751) as described previously (39). This study subsequently found no significant effect of this compound on fibrosis or stellate cell activation after 12 months. Plasma samples were available from a subpopulation of 194 patients with CHC genotype 1 infection and compensated liver disease with Ishak fibrosis stage 2-4. 131 patients received 0.5 or 1.0 mg farglitazar twice a day and 63 received matching placebo for 52 weeks. Liver biopsies at baseline and 52 weeks were reviewed by a single experienced histopathologist using the Ishak modified histologic activity index (HAI) for grading and staging (40). These methods and specimen quality measures have been described in detail previously (39). The controls were derived from a previously described study (41,42). This study was approved by the Duke University Institutional Review Board.

Type III collagen formation was assessed in all baseline plasma samples from CHC patients and healthy controls using the herein described competitive ELISA for PIIINP ("Pro-C3").

Baseline Plasma Pro-C3 in Healthy Controls and CHC Patients

No difference between treated patients and placebo was observed for Pro-C3 (p=0.299) (data not shown). Pro-C3 levels showed an overall significant difference in all group comparisons for Ishak stage 2, 3 and 4 (p<0.001) (FIG. 7). Pro-C3 levels were increased in Ishak stage 4 compared to stage 2 (p<0.05) or stage 3 (p<0.05).

The diagnostic value of Pro-C3 for separation of healthy and CHC patients was performed using ROC analysis. The AUC was 0.82 (p<0.001) and 0.91 (p<0.001) for distinguishing controls from patients with mild (Ishak stage 2 and 3) and moderate (stage 4) fibrosis, respectively (FIGS. 8A-8B). AUC for differentiating mild from moderate fibrosis stages was 0.72 (p<0.001) for Pro-C3 (FIG. 8C). Controls and CHC patients were further divided into quartiles according to their Pro-C3 plasma level. The odds ratios (OR) for differentiating controls from CHC patients was calculated for each quartile (Q) (FIG. 8D): Q1 was set to an OR=1, Q2: OR=4.1 [95% CI 1.4-12.1], Q3: OR=21.6 [95% CI 2.7-169.7], and Q4 included only CHC patients.

These results demonstrate a clear ability of the Pro-C3 immunoassay to distinguish between healthy and CHC patients.

Association Between Baseline Plasma Pro-C3 and Progression of Disease

The association between baseline biomarker levels and regression or progression of disease after 52 weeks was investigated by comparing the patients with a decrease of 1 in Ishak stage (group −1, n=20), the stable patients (group 0, n=103), the patients with an increase of 1 (group 1, n=30) and with an increase of 2 in Ishak stage (group 2, n=6). There was an overall difference in baseline Pro-C3 mean levels (p=0.005) between the four groups (FIG. 9). Pro-C3 levels were significantly higher in group 1 compared to group −1 (p=0.049) and for group 2 compared to both −1 (p=0.012) and 0 (p=0.037) (FIG. 9).

The prognostic value of Pro-C3 for disease progression was investigated in the different baseline Ishak stages 2, 3 and 4. Patients in each stage were classified as "progressors" (n=36) or "stable" (n=103) and means were calculated. Plasma Pro-C3 levels were significantly elevated for progressors compared to stable CHC patients in Ishak 2 (p=0.014) and Ishak 3 (p=0.020). There were no significant differences for Ishak 4 (Data not shown). ROC analysis of the Pro-C3 prognostic value was performed (FIG. 10A), yielding an AUC of 0.63 (p=0.030), when stable patients were compared to progressors. For differentiating progressors from stable patients the OR was calculated in the Pro-C3 quartiles (Q): Q1 was set to OR=1, Q2: OR=1.0 [95% CI 0.28-3.63], Q3: OR=1.5 [95% CI 0.48-4.72], and Q4: OR=3.4 [95% CI 1.21-9.69] (p=0.015) (FIG. 10B).

These results demonstrate the prognostic ability of the Pro-C3 immunoassay for detecting CHC patients whose condition is deteriorating (i.e. liver fibrosis is increasing), or likely to deteriorate, particularly for patients with an Ishak score of 2 or 3. Specifically, patients of a given Ishak score that have a Pro-C3 value of above the statistical second quartile (>Q2) for that Ishak score will likely have a deteriorating condition. This is particularly useful information when selecting patients for pharmaceutical trials and/or when prescribing drug therapy as the level of false results based on patients "responding" to preventative treatment may be reduced by eliminating patients who would not have deteriorated without treatment.

Example 8

PRO-C3 ELISA for Assessment of Liver Fibrosis

The clinical utility, i.e. sensitivity and specificity, of the PRO-C3 ELISA in patients with liver fibrosis was investigated in two study populations, i.e. patients with chronic hepatitis B (HBV) infection and another group of patients with chronic hepatitis C (HCV) infection.
Patients and Methods
Patients with HBV and HCV
A cross-sectional study in 189 patients with chronic HBV infection and 375 patients with chronic HCV infection was conducted. Presence and severity of liver fibrosis was evaluated using liver biopsies as described below.

Briefly, 96-well pre-coated streptavidin plates (Roche Diagnostics, Mannheim, Del.) were coated with the appropriate biotinylated synthetic peptides (biotin-CGG-CPTG-PQNYSP (SEQ ID NO: 11)) and incubated for 30 minutes at 20° C. 20 μL of standard peptide (CPTGPQNYSP (SEQ ID NO: 6)) or pre-diluted sample were added to appropriate wells, followed by 100 μL of peroxidase-conjugated specific monoclonal antibodies and incubated for 1 hour or overnight at 20° C. or 4° C., respectively. Finally, 100 μL tetramethylbenzidine (TMB) (cat.4380H, Kem-En-Tec Diagnostics, Taastrup, Denmark) was added, and the plates were incubated for 15 minutes at 20° C. in the dark. All the above incubation steps included shaking at 300 rpm. After each incubation step, the plate was washed five times in washing buffer (20 mM Tris, 50 mM NaCl, pH 7.2). The TMB reaction was stopped by adding 100 μL of stopping solution (0.18 M H2SO4) and measured at 450 nm with 650 nm as the reference. A calibration curve was plotted using a 4-parametric mathematical fit model.

The stained liver biopsies were examined by experienced pathologists and scored according to the Metavir scoring system for the stage of fibrosis (f0-f4). This system assesses histologic lesions in the liver and the scores are defined as follows:
 f0: no fibrosis
 f1: portal fibrosis without septa
 f2: portal fibrosis with rare septa
 f3: numerous septa without cirrhosis
 f4: cirrhosis Data were logarithmically transformed to obtain normality and symmetry of variance. Comparisons between the mean marker levels stratified according to F-score were performed using one-way Analysis of Variance (ANOVA) test with Tukey's multiple comparisons test using each group as fixed factor. Correlations were calculated as the Pearson Rho coefficient. Data are shown as geometric mean±standard error of the mean (SEM). P-values less than 5% were considered significant. All statistical analyses were calculated in MedCalc® version 12 (MedCalc Software, Ostend, Belgium) and graphs were designed using GraphPad Prism® version 5 (GraphPad Software, Inc., CA, USA).
Patients with HBV Infection First, the demographic data and the PRO-C3 data were summarized according to Metavir F score (Table 6). By ANOVA statistics it was demonstrated that PRO-C3 test results classified according to Metavir score differed significantly with liver fibrosis (p<0.001). After adjustment for the co-variables age and BMI this relationship remained significant (data not shown). In contrast, the degree of liver fibrosis as assessed by Metavir score did not show a significant relation to age, BMI and gender.

TABLE 6

Demographics and PRO-C3 Results According to Metavir F-score.

| HBV | n | METAVIR F stage 0 | n | 1 | n | 2 | n | 3 | n | 4 | ANOVA p |
|---|---|---|---|---|---|---|---|---|---|---|---|
| Mean age (year SD) | 39 | 41.0 (9.9) | 95 | 40.3 (11.9) | 35 | 44.5 (11.1) | 16 | 37.4 (12.8) | 4 | 51.7 (15.0) | 0.080 |
| BMI (±SEM) | 39 | 23.9 (23.3-24.6) | 95 | 24.1 (23.8-24.5) | 35 | 24.6 (23.9-25.3) | 16 | 23.8 (22.6-25.1) | 4 | 24.7 (21.8-28.0) | 0.962 |
| Male (%) | 20 | 51% | 58 | 61% | 24 | 69% | 13 | 81% | 3 | 75% | 0.253 |
| PRO-C3 (±SEM) | 39 | 18.2 (16.8-19.6) | 95 | 19.6 (18.8-20.4) | 35 | 24.9 (23.1-26.8) | 16 | 37.8 (32.6-43.8) | 4 | 27.2 (18.0-41.1) | <0.001 |

Age followed a normal distribution and is reported as geometric mean with standard deviation. BMI and PRO-C3, however, did not follow a normal distribution and are reported as geometric mean±SEM.

In a graphic representation of the same data (FIG. 11), the association of the liver fibrosis score with the PRO-C3 assessment in EDTA plasma was clearly observed. Due to the low number of patients with Metavir F score 4 (n=4), this group was merged with Metavir F score 3.

Clinically, the most important decision point is the ability to detect liver fibrosis in its early stages. Therefore, the ability of the PRO-C3 to distinguish patients with Metavir F score 0-1 from the more advanced stages (score 2-4), was investigated. A ROC analysis demonstrated that using a cut off of 19.21 ng/mL for PRO-C3, the test had a sensitivity and specificity of 76.4 and 61.7%, respectively (Table 7). The ability to distinguish early from moderate to late liver fibrosis was statistically highly significant (p<0.0001). Positive and negative predicted values for PRO-C3 were in the range 44-57% (Table 7).

TABLE 7

PRO-C3: ROC Analysis on Metavir F score

| PRO-C3 HBV Group | Sensitivity (%) | Specificity (%) | AUC | P-value | PPV (%) | NPV (%) | Cut off (ng/mL) |
|---|---|---|---|---|---|---|---|
| Early (0-1) vs moderate-late (2-4) | 76.4 | 61.9 | 0.728 | <0.0001 | 56.5 | 44.2 | >19.21 |

PPV: Positive predictive value; NPV: Negative predictive value.

Patients with HCV Infection

Demographic and PRO-C3 data are summarized according to Metavir F score in the table below (Table 8). By ANOVA statistics, it was demonstrated that PRO-C3 test results differed significantly with liver fibrosis as assessed by Metavir F score. In this study population, severity of liver fibrosis was associated with both older age and increased BMI, however, the association between PRO-C3 and the Metavir score remained significant even after adjustment with the co-variables age and BMI (data not shown).

TABLE 8

Demographics and PRO-C3 Results According to Metavir F-score

| HCV | n | METAVIR F stage 0 | n | 1 | n | 2 | N | 3 | n | 4 | ANOVA p |
|---|---|---|---|---|---|---|---|---|---|---|---|
| Mean age Year (SD) | 42 | 39.0 (9.8) | 156 | 41.8 (10.4) | 99 | 45.7 (8.7) | 45 | 47.5 (9.2) | 33 | 49.1 (6.6) | <0.001 |
| BMI (±SEM) | 42 | 25.2 (24.6-25.8) | 156 | 25.6 (25.2-25.9) | 99 | 26.8 (26.3-27.4) | 45 | 27.8 (27.1-28.5) | 33 | 26.6 (26.0-27.3) | 0.015 |
| Male sex | 23 | 55% | 86 | 55% | 67 | 68% | 33 | 73% | 21 | 64% | 0.100 |
| PRO-C3 (±SEM) | 42 | 17.5 (16.7-18.3) | 156 | 19.9 (19.2-20.4) | 99 | 24.3 (23.3-25.4) | 45 | 36.4 (33.7-39.3) | 33 | 41.2 (37.8-45.0) | <0.001 |

Age followed a normal distribution and is reported as geometric mean with standard deviation. BMI and PRO-C3, however, did not follow a normal distribution and are reported as geometric mean±SEM.

In a graphic representation of the data (FIG. 12), the association of the liver fibrosis score with the PRO-C3 assessments in plasma was clearly observed. ROC analysis demonstrated that using a cut-off of 22.21 ng/mL for PRO-C3, the test had a sensitivity and specificity of 68.4 and 72.6%, respectively (Table 4). The ability to distinguish early from moderate to late liver fibrosis was statistically highly significant (p<0.0001). Positive and negative predicted values for PRO-C3 were in the range 49-51% (Table 9).

TABLE 9

PRO-C3: ROC Analysis on Metavir F score

| PRO-C3 HCV Group | Sensitivity (%) | Specificity (%) | AUC | P-value | PPV (%) | NPV (%) | Cut off (ng/mL) |
|---|---|---|---|---|---|---|---|
| Early (0-1) vs moderate-late (2-4) | 68.4 | 72.7 | 0.758 | <0.0001 | 49.4 | 51.4 | >22.21 |

PPV: Positive predictive value; NPV: Negative predictive value.

Example 9

PRO-C3X Assay

As noted above, enzymatic collagen crosslinking by lysyl oxidases (LOXs) and processing of pro-collagens is key for tissue maturation and stability. Thus, monitoring inter-strand cross-linking of pro-collagen type III prior to enzymatic processing may prove useful for monitoring in-vivo activity of LOXs. This can be achieved by detecting and quantifying cross-linked PIIINP (i.e. two or more strands of PIIINP bound together by inter-strand links formed by LOXs in pro-collagen type III prior to enzymatic processing of the pro-collagen). A higher level of cross-linked PIIINP detected in the circulation would be indicative of greater LOX activity. Accordingly, monitoring the level of cross-linked PIIINP during drug trials for drugs targeting LOX, such as LOX antagonists, could provide useful efficacy data for said drugs.

ELISA

Streptavidin-coated plates were coated with 100 μl/well of 1 μg/ml biotinylated catcher antibody (biotin-linked NB61-N62) and incubated at 20° C., 300 rpm shaking for 30 minutes. Plates were washed five times in washing buffer (20 nM TRIS, 50 mM NaCl, pH 7.2). Sample, standard or control (20 μl) was added and followed immediately by addition of 100 μl assay buffer and incubated at 4° C., 300 rpm shaking for 20 hours. After incubation, plates were washed five times in washing buffer. 100 μl/well of 1 μg/ml HRP-labelled detector antibody (HRP-linked NB61-N62) was added and incubated at 20° C., 300 rpm, shaking for 1 hour. After incubation, plates were washed five times in washing buffer. A volume of 100 μl 3,3',5,5'-Tetramethylbenzidine (TMB) was added and incubated for 15 min at 20° C. in the dark. To stop the enzyme reaction of TMB, 100 μl 0.1% sulphuric acid was added. The enzyme reaction was then read on an ELISA reader, using a quadratic curve fit. Each ELISA plate included both kit control and in-house quality control samples to monitor inter-assay variation. All samples were measured within the range of the specific assay. All samples below the level of lower limited of quantification (LLOQ) were assigned the value of LLOQ.

The technical characteristics of the assay are:

| Parameter | Results |
|---|---|
| Biological matrix | Serum, plasma, supernatants, extraction fluid. |
| Intra-assay variation | 2% (accepted if <10%) |
| Inter-assay variation | 6% (accepted if <15%) |
| Measurement range | 0.965-17.586 ng/ml |
| Lower limit of detection | 0.251 ng/ml |
| Normal range in healthy serum | 4.022 (±2.24) ng/ml |
| Required volume | 30 µl serum/plasma; 60 µl supernatant/extraction |
| Spiking recovery | Peptide in serum: 94% Serum in serum: 86% |

Results
Scar Tissue

Preliminary results using an in vitro model of lung fibroblasts ("scar-in-a-jar") strongly suggest that an enzyme of the LOX family is the responsible for the cross-link in PIIINP (TGF-β is known in the art to increase lysyl oxidase (LOX) enzyme activity). Briefly, Pro-C3X (i.e. cross-linked PIIINP) was generated by culturing lung fibroblasts for 5 days in crowded conditions and under TGF-β stimulation. Pro-C3X was significantly elevated after 12 days of culturing with TGF-β, with negligible quantities of Pro-C3X being observed in the absence of TGF-β (FIG. 13). Similarly, Pro-C3X was elevated in extractions from keloids when compared to extractions from normal skin (FIG. 14).

Liver Fibrosis

A study of patients with liver fibrosis was conducted using the "Pro-C3X" assay and compared to the herein described "Pro-C3" competitive ELISA. It was found that Pro-C3X was significantly elevated in later stages of disease, when fibrosis is more severe, with levels similar to healthy controls in early stages of disease (FIG. 15A). In comparison, Pro-C3 levels differed at all stages of the disease (FIG. 15B).

The difference in selectivity between the Pro-C3X and Pro-C3 assay is attributed to the Pro-C3X assay only recognizing cross-linked PIIINP, whereas the Pro-C3 assay recognises both cross-linked and non-cross-linked PIIINP. FIG. 16 shows the Pro-C3X assay and provides a pictorial explanation for the reasoning behind this conclusion:

Pro-C3X assay: if cross linked PIIINP is present then the first antibody will bind to the free epitope on a first strand of PIIINP and subsequently the second antibody will bind to the free epitope on a second strand of PIIINP. However, if non-cross-linked PIIINP is present then the surface-bound antibody will bind to the free epitope of the non-cross linked collagen type III, but the second antibody will fail to bind as the binding epitope is already occupied, therefore addition of the second antibody will fail to produce a signal. Thus, the signal from the Pro-C3X assay is exclusively due to the detection of cross linked PIIINP.

Conversely, substantially all of the antibodies in the Pro-C3 assay will bind to strands of PIIINP comprising a free binding epitope, irrespective of whether the PIIINP is or is not cross-linked. Thus, the signal obtained from the Pro-C3 assay is an aggregate signal of cross-linked and non-cross-linked PIIINP.

Accordingly, it is this selectivity that prompts the use of the Pro-C3X assay for evaluating the efficacy of drugs targeting LOX; monitoring the level of PIIINP cross-linking which, as noted above, is suggested to be a result of LOX activity during a period of drug administration to a subject could be used to monitor drug activity and thus efficacy of said drug.

Alcoholic Steatohepatitis

A study of patients with alcoholic steatohepatitis was conducted using the "Pro-C3X" assay and compared to the herein described "Pro-C3" assay. In alcoholic steatohepatitis, both Pro-C3 and Pro-C3X were elevated in later stages of the disease (Metavir 2-4). However, for patients with cirrhosis Pro-C3 did not correlate with MELD (Model For End-Stage Liver Disease) score (P=0.527), whereas Pro-C3X strongly correlated (corr coefficient 3.34, P<0.001). Moreover, ProC3 only correlated negatively with albumine, while ProC3X correlated with albumine, bilirubine and Gamma-Glutamyl Transpeptidase (GGT) (FIG. 17). The late stage increase in Pro-C3X suggests increase in cross-linking of PIIINP, which would be in accordance with increased scarring of the liver (i.e. increased LOX activity).

In conclusion, the Pro-C3X assay is a second generation assay combining the cleavage neo-epitope of the collagen type III pro-peptide and the presence of cross-linking in the molecule. This assay is therefore providing additional information to the measurement of Pro-C3, because it describes a different process in the fibrosis timeline; that is, the cross-linking of collagen molecules in the scar. The Pro-C3X assay could therefore be used to test the efficacy of drugs targeting LOX, particularly LOX antagonists/inhibitors, since the use of an inhibitor would likely reduce the presence of the cross-linked PIIINP biomarker.

In this specification, unless expressly otherwise indicated, the word 'or' is used in the sense of an operator that returns a true value when either or both of the stated conditions is met, as opposed to the operator 'exclusive or' which requires that only one of the conditions is met. The word 'comprising' is used in the sense of 'including' rather than in to mean 'consisting of'. All prior teachings acknowledged above are hereby incorporated by reference. No acknowledgement of any prior published document herein should be taken to be an admission or representation that the teaching thereof was common general knowledge in Australia or elsewhere at the date hereof.

The following references are cited herein:
1. World Health Organization. Reducing Risks, Promoting Healthy Life. Peducing Risks, Promoting Healthy Life, Geneva: WHO, 2002:1-230.
2. Wynn T A. Cellular and molecular mechanisms of fibrosis. J Pathol 2008; 214:199-210.
3. Friedman S L. Mechanisms of disease: Mechanisms of hepatic fibrosis and therapeutic implications. Nat Clin Pract Gastroenterol Hepatol 2004; 1:98-105.
4. Tomasek J, Gabbiani G, Hinz B, Chaponnier C, Brown R A. Myofibroblasts and mechano-regulation of connective tissue remodelling. Nat Rev Mol Cell Biol 2002; 3:349-363.
5. Wynn T A. Common and unique mechanisms regulate fibrosis in various fibroproliferative diseases. J Clin Invest 2007; 117:524-529.
6. Bosman, F. T., and Stamenkovic, I. 2003. Functional structure and composition of the extracellular matrix. *J. Pathol.* 200:423-428.
7. Bruckner, P. 2010. Suprastructures of extracellular matrices: paradigms of functions controlled by aggregates rather than molecules. *Cell Tissue Res.* 339:7-18.

8. Bao X, Zeng Y, Wei S, Wang G, Liu C, Sun Y, Chen Q, and Li H. Developmental changes of Col3a1 mRNA expression in muscle and their association with intramuscular collagen in pigs. J Genet Genomics 2007; 34(3): 223-228.
9. Jensen L T and Host N B. Collagen: scaffold for repair or execution. Cardiovasc Res 1997; 33(3): 535-539.
10. Niemela O, Risteli L, Parkkinen J, and Risteli J. Purification and characterization of the N-terminal propeptide of human type III procollagen. Biochem J 1985; 232(1): 145-150.
11. Wang W M, Ge G, Lim N H, Nagase H, and Greenspan D S. TIMP-3 inhibits the procollagen N-proteinase ADAMTS-2. Biochem J 2006; 398(3): 515-519.
12. Van den Steen P E, Opdenakker G, Wormald M R, Dwek R A, and Rudd P M. Matrix remodelling enzymes, the protease cascade and glycosylation. Biochim Biophys Acta 2001; 1528(2-3): 61-73.
13. Cuzner M L and Opdenakker G. Plasminogen activators and matrix metalloproteases, mediators of extracellular proteolysis in inflammatory demyelination of the central nervous system. J Neuroimmunol 1999; 94(1-2): 1-14.
14. Meduri G U, Tolley E A, Chinn A, Stentz F, and Postlethwaite A. Procollagen types I and III aminoterminal propeptide levels during acute respiratory distress syndrome and in response to methylprednisolone treatment. Am J Respir Crit Care Med 1998; 158(5 Pt 1): 1432-1441.
15. Teare J P, Sherman D, Greenfield S M, Simpson J, Bray G, Catterall A P, Murray-Lyon I M, Peters T J, Williams R, and Thompson R P. Comparison of serum procollagen III peptide concentrations and PGA index for assessment of hepatic fibrosis. Lancet 1993; 342(8876): 895-898.
16. Scheja A, Akesson A, and Horslev-Petersen K. Serum levels of aminoterminal type III procollagen peptide and hyaluronan predict mortality in systemic sclerosis. Scand J Rheumatol 1992; 21(1): 5-9.
17. Lin Y H, Ho Y L, Wang T D, Liu C P, Kao H L, Chao C L, Chien K L, Hung C S, Wu V C, Tsai I J, Yen R F, Shiau Y C, and Chen W J. The relation of amino-terminal propeptide of type III procollagen and severity of coronary artery disease in patients without myocardial infarction or hibernation. Clin Biochem 2006; 39(9): 861-866.
18. Teppo A M, Tornroth T, Honkanen E, and Gronhagen-Riska C. Urinary amino-terminal propeptide of type III procollagen (PIIINP) as a marker of interstitial fibrosis in renal transplant recipients. Transplantation 2003; 75(12): 2113-2119.
19. Han X Y, Wang W, Komulainen J, Koskinen S O, Kovanen V, Vihko V, Trackman P C, and Takala T E. Increased mRNAs for procollagens and key regulating enzymes in rat skeletal muscle following downhill running. Pflugers Arch 1999; 437(6): 857-864.
20. Koskinen S O, Ahtikoski A M, Komulainen J, Hesselink M K, Drost M R, and Takala T E. Short-term effects of forced eccentric contractions on collagen synthesis and degradation in rat skeletal muscle. Pflugers Arch 2002; 444(1-2): 59-72.
21. Crameri R M, Langberg H, Teisner B, Magnusson P, Schroder H D, Olesen J L, Jensen C H, Koskinen S, Suetta C, and Kjaer M. Enhanced procollagen processing in skeletal muscle after a single bout of eccentric loading in humans. Matrix Biol 2004; 23(4): 259-264.
22. Chen F, Lam R, Shaywitz D, Hendrickson R C, Opiteck G J, Wishengrad D, Liaw A, Song Q, Stewart A J, Cummings C E, Beals C, Yarasheski K E, Reicin A, Ruddy M, Hu X, Yates N A, Menetski J, and Herman G A. Evaluation of early biomarkers of muscle anabolic response to testosterone. J Cachexia Sarcopenia Muscle 2011; 2(1): 45-56.
23. Longobardi S, Keay N, Ehrnborg C, Cittadini A, Rosen T, Dall R, Boroujerdi M A, Bassett E, Healy M L, Pentecost C, Wallace J D, Powrie J, Jorgensen J O, and Sacca L. Growth hormone (G H) effects on bone and collagen turnover in healthy adults and its potential as a marker of G H abuse in sports: a double blind, placebo-controlled study. The GH-2000 Study Group. J Clin Endocrinol Metab 2000; 85(4): 1505-1512.
24. Bhasin S, He E J, Kawakubo M, Schroeder E T, Yarasheski K, Opiteck G J, Reicin A, Chen F, Lam R, Tsou J A, Castaneda-Sceppa C, Binder E F, Azen S P, and Sattler F R. N-terminal propeptide of type III procollagen as a biomarker of anabolic response to recombinant human G H and testosterone. J Clin Endocrinol Metab 2009; 94(11): 4224-4233.
25. Nelson A E, Meinhardt U, Hansen J L, Walker I H, Stone G, Howe C J, Leung K C, Seibel M J, Baxter R C, Handelsman D J, Kazlauskas R, and Ho K. Pharmacodynamics of growth hormone abuse biomarkers and the influence of gender and testosterone: a randomized double-blind placebo-controlled study in young recreational athletes. J Clin Endocrinol Metab 2008; 93(6): 2213-2222.
26. Zachariae H, Heickendorff L, and Sogaard H. The value of amino-terminal propeptide of type III procollagen in routine screening for methotrexate-induced liver fibrosis: a 10-year follow-up. Br J Dermatol 2001; 144(1): 100-103.
27. Gressner A M and Weiskirchen R. Modern pathogenetic concepts of liver fibrosis suggest stellate cells and TGF-beta as major players and therapeutic targets. J Cell Mol Med 2006; 10(1): 76-99.
28. Jarcuska P, Janicko M, Veseliny E, Jarcuska P, and Skladany L. Circulating markers of liver fibrosis progression. Clin Chim Acta 2010; 411(15-16): 1009-1017.
29. Frei A, Zimmermann A, and Weigand K. The N-terminal propeptide of collagen type III in serum reflects activity and degree of fibrosis in patients with chronic liver disease. Hepatology 1984; 4(5): 830-834.
30. Fabris P, Marranconi F, Bozzola L, Biasin M R, De Lazzari F, Plebani M, Benedetti P, Tositti G, Pellizzer G, Stecca C, and de L F. Fibrogenesis serum markers in patients with chronic hepatitis C treated with alpha-IFN. J Gastroenterol 1999; 34(3): 345-350.
31. Brocks D G, Steinert C, Gerl M, Knolle J, Neubauer H P, and Gunzler V. A radioimmunoassay for the N-terminal propeptide of rat procollagen type III. Application to the study of the uptake of the N-terminal propeptide of procollagen type III in isolated perfused rat liver. Matrix 1993; 13(5): 381-387.
32. Rohde H, Vargas L, Hahn E, Kalbfleisch H, Bruguera M, and Timpl R. Radioimmunoassay for type III procollagen peptide and its application to human liver disease. Eur J Clin Invest 1979; 9(6): 451-459.
33. Bayer Aktiengesellschaft. (1999) Monoclonal antibody and assay for detecting PIIINP. Patent Cooperation Treaty Appn. WO 99/61477.
34. Warming L, Hassager C, and Christiansen C. Changes in bone mineral density with age in men and women: a longitudinal study. Osteoporos Int 2002; 13(2): 105-112.
35. Segovia-Silvestre T, Reichenbach V, Fernandez-Varo G, Vassiliadis E, Barascuk N, Morales-Ruiz M, Karsdal M A, and Jimenez W. Circulating CO3-610, a degradation product of collagen III, closely reflects liver collagen and portal pressure in rats with fibrosis. Fibrogenesis Tissue Repair 2011; 4: 19
36. Cláraia J and Jiménez W. Experimental Models of Cirrhosis and Ascites. 2005; Second edition(17)
37. Schuppan D, Ruehl M, Somasundaram R, and Hahn E G. Matrix as a modulator of hepatic fibrogenesis. Semin Liver Dis 2001; 21(3): 351-372.
38. Suetta C, Hvid L G, Justesen L, Christensen U, Neergaard K, Simonsen L, Ortenblad N, Magnusson S P, Kjaer M, and Aagaard P. Effects of aging on human skeletal muscle after immobilization and retraining. J Appl Physiol 2009; 107(4): 1172-1180.
39. McHutchison J, Goodman Z, Patel K, Makhlouf H, Rodriguez-Torres M, Shiffman M, et al. Farglitazar lacks antifibrotic activity in patients with chronic hepatitis C infection. Gastroenterology 2010 April; 138(4): 1365-73, 1373.
40. Ishak K, Baptista A, Bianchi L, Callea F, De G J, Gudat F, et al. Histological grading and staging of chronic hepatitis. J Hepatol 1995 June; 22(6):696-699.
41. Warming L, Hassager C, Christiansen C. Changes in bone mineral density with age in men and women: a longitudinal study. Osteoporos Int 2002; 13(2):105-112.
42. Mouritzen U, Christgau S, Lehmann H J, Tanko L B, Christiansen C. Cartilage turnover assessed with a newly developed assay measuring collagen type II degradation products: influence of age, sex, menopause, hormone replacement therapy, and body mass index. Ann Rheum Dis 2003 April; 62(4):332-336.

What is claimed is:

1. A sandwich immunoassay for detecting in a biological sample cross-linked PIIINP, said cross-linked PIIINP comprising at least two strands of PIIINP joined together by inter-strand cross-linking, said method comprising:
   contacting said biological sample comprising said cross-linked PIIINP with a first monoclonal antibody bound to a surface, wherein each strand of PIIINP comprised in the cross-linked PIIINP comprises a C-terminal neo-epitope of PIIINP generated by N-protease cleavage of intact type III procollagen;
   adding a second monoclonal antibody; and
   determining the amount of binding of said second monoclonal antibody;
   wherein said first monoclonal antibody is specifically reactive with said C-terminal neo-epitope in a first strand of PIIINP and said second monoclonal antibody is specifically reactive with said C-terminal neo-epitope in a second strand of PIIINP, wherein said first and second strands of PIIINP are joined together by inter-strand cross-linking, and wherein said C-terminal neo-epitope is comprised in a C-terminal amino acid sequence CPTGXQNYSP-COOH (SEQ ID NO: 4), wherein X is Gly or Pro.

2. The sandwich immunoassay of claim 1, wherein the first monoclonal antibody and the second monoclonal antibody do not substantially recognise or bind an elongated version of said C-terminal amino acid sequence which is CPTGXQNYSPQZ-COOH (SEQ ID NO: 5), wherein Z is absent or is one or more amino acids of the sequence of collagen type III.

3. The sandwich immunoassay of claim 1, wherein the sandwich immunoassay is used to quantify the amount of cross-linked PIIINP in a biological sample.

4. The sandwich immunoassay of claim 3, further comprising correlating the quantity of cross-linked PIIINP determined by said method with standard fibrotic disease samples of known disease severity to evaluate the severity of said known fibrotic disease.

5. The sandwich immunoassay of claim 4, wherein the fibrotic disease is liver disease.

6. The sandwich immunoassay of claim 3, wherein the biological sample is a biofluid.

7. The sandwich immunoassay of claim 6, wherein said biofluid is serum, plasma, urine, amniotic fluid, tissue supernatant or cell supernatant.

8. The sandwich immunoassay of claim 1, wherein the sandwich immunoassay is a radioimmunoassay, fluorescence immunoassay, or an enzyme-linked immunosorbent assay.

9. The sandwich immunoassay of claim 1, wherein the second monoclonal antibody is labeled.

10. The sandwich immunoassay of claim 9, wherein the second monoclonal antibody is an enzyme-linked antibody.

11. The sandwich immunoassay of claim 10, wherein the enzyme is horseradish peroxidase (HRP).

12. The sandwich immunoassay of claim 9, wherein the second monoclonal antibody is radiolabeled or linked to a fluorophore.

13. The sandwich immunoassay of claim 1, wherein a further labeled antibody which recognises the second monoclonal antibody is used to determine the amount of binding of said second monoclonal antibody.

14. A kit for use in a sandwich assay, the kit comprising:
   a solid support to which is bound the first monoclonal antibody as defined in claim 1; and
   the second monoclonal antibody as defined in claim 1, said second monoclonal antibody comprising a label.

* * * * *